(12) United States Patent
Fowler et al.

(10) Patent No.: US 7,974,380 B2
(45) Date of Patent: Jul. 5, 2011

(54) METHOD AND SYSTEM FOR CRYSTALLIZATION AND X-RAY DIFFRACTION SCREENING

(75) Inventors: Brian Fowler, San Mateo, CA (US); Andrew May, San Francisco, CA (US)

(73) Assignee: Fluidigm Corporation, South San Francisco, CA (US)

( * ) Notice: Subject to any disclaimer, the term of this patent is extended or adjusted under 35 U.S.C. 154(b) by 276 days.

(21) Appl. No.: 12/118,185

(22) Filed: May 9, 2008

(65) Prior Publication Data

US 2009/0147918 A1  Jun. 11, 2009

Related U.S. Application Data

(60) Provisional application No. 60/928,865, filed on May 11, 2007, provisional application No. 60/928,649, filed on May 9, 2007.

(51) Int. Cl.
 *G01N 23/20* (2006.01)
(52) U.S. Cl. .......................................... 378/79; 378/208
(58) Field of Classification Search ............. 378/79, 378/86, 208; 117/68
See application file for complete search history.

(56) References Cited

U.S. PATENT DOCUMENTS

| 6,408,878 | B2 | 6/2002 | Unger et al. | |
|---|---|---|---|---|
| 6,719,840 | B2 | 4/2004 | David et al. | |
| 6,793,753 | B2 | 9/2004 | Unger et al. | |
| 6,849,459 | B2 * | 2/2005 | Gilbert et al. | 436/86 |
| 7,195,670 | B2 | 3/2007 | Hansen et al. | |
| 7,704,735 | B2 * | 4/2010 | Facer et al. | 435/303.1 |
| 2003/0061687 | A1 | 4/2003 | Hansen et al. | |
| 2004/0072278 | A1 * | 4/2004 | Chou et al. | 435/29 |
| 2005/0062196 | A1 | 3/2005 | Hansen et al. | |
| 2005/0214173 | A1 | 9/2005 | Facer et al. | |
| 2006/0246493 | A1 | 11/2006 | Jensen et al. | |
| 2006/0281183 | A1 * | 12/2006 | Sun et al. | 436/43 |

FOREIGN PATENT DOCUMENTS

| WO | WO 2004/104228 | 12/2004 |
|---|---|---|
| WO | WO 2005/056813 | 6/2005 |
| WO | WO 2008/043046 | 4/2008 |

OTHER PUBLICATIONS

International Search Report and Written Opinion of PCT Application No. PCT/US2008/06324, mailed Aug. 21, 2008, 11 pages.

* cited by examiner

*Primary Examiner* — Chih-Cheng G Kao
(74) *Attorney, Agent, or Firm* — Kilpatrick Townsend & Stockton LLP

(57) ABSTRACT

An integrated fluidic circuit includes a substrate layer and a first structure coupled to the substrate layer and including a plurality of channels. The first structure is configured to provide for flow of one or more materials through the plurality of channels. The integrated fluidic circuit also includes a second structure coupled to the substrate layer. The second structure includes a plurality of control channels configured to receive an actuation pressure. The integrated fluidic circuit is characterized by a thickness of less than 1.5 mm.

26 Claims, 10 Drawing Sheets

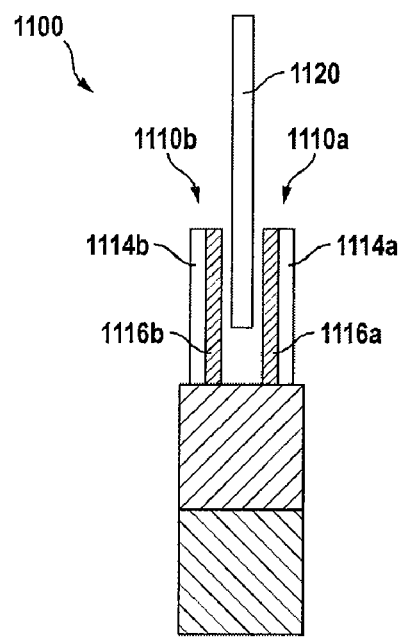
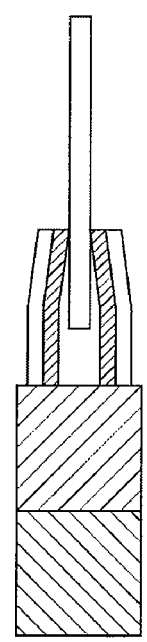
FIG. 11A    FIG. 11B
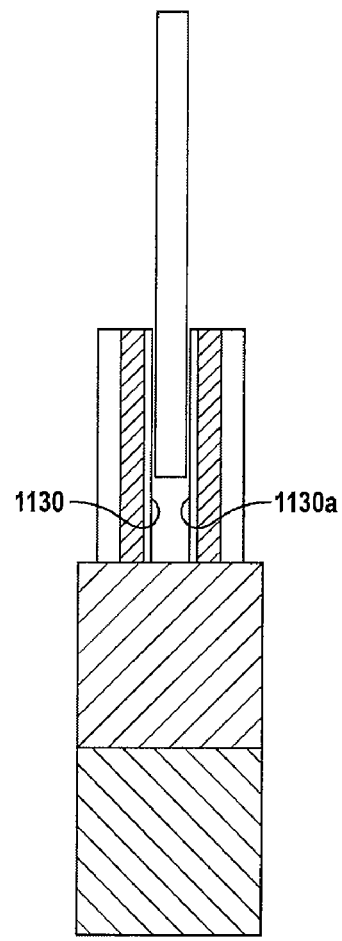
FIG. 11C

METHOD AND SYSTEM FOR CRYSTALLIZATION AND X-RAY DIFFRACTION SCREENING

CROSS-REFERENCES TO RELATED APPLICATIONS

The present application claims benefit under 35 U.S.C. §119(e) of U.S. Provisional Patent Application No. 60/928,649, filed on May 9, 2007, entitled "In situ crystallography," and U.S. Provisional Patent Application No. 60/928,865, filed on May 11, 2007, entitled "In situ crystallography," the disclosures of which are hereby incorporated by reference in their entirety for all purposes.

STATEMENT AS TO RIGHTS TO INVENTIONS MADE UNDER FEDERALLY SPONSORED RESEARCH OR DEVELOPMENT

Work described herein has been supported, in part, by NIH/NIGMS STTR Phase II Grant No. 2R42GM071326-02A1. The United States Government may therefore have certain rights in the invention.

BACKGROUND OF THE INVENTION

The present invention relates generally to nanofluidic systems. In particular, the invention provides an architecture including nanovolume crystallization chambers configured for use in x-ray crystallographic diffraction analysis systems. More particularly, the present method and system provides for a low volume crystallization chamber with reduced x-ray scattering suitable for in-situ crystallography. Merely by way of example, the nanofluidic methods and systems described herein have been applied to a chip geometry that supports crystal growth from reduced volumes and features carbon-based elastomers and non-elastomers in layers through which the x-ray beam passes. Although the techniques for nanofluidic systems are applied to x-ray diffraction analysis of macromolecular crystals, it would be recognized that the invention has a much broader range of applicability.

X-ray diffraction of macromolecular crystals is a method relied upon to determine the ternary structure of native proteins, nucleic acids, or protein-ligand complexes. Obtaining useful X-ray diffraction data, however, is complicated by the difficulty of growing diffraction-quality crystals, the mechanical fragility of macromolecular crystals and the accompanying care with which the crystals must be handled, and the innate interference of the device and milieu suspending the macromolecular crystal in the X-ray beam. Current processes for performing all of the steps from crystallization to successful diffraction are complex and time consuming.

Various microvolume apparatus have been developed to screen conditions and reagents for crystallizing proteins from solution. One such apparatus is the TOPAZ® 1.96 screening chip, available from the present assignee, which utilizes microvolume chambers formed in an elastomeric structure that are filled, isolated, and then interfaced to allow combinations of protein solutions to interact with crystallizing reagents through free interface diffusion. Low volume chambers with microfluidic architecture provide for large scale screening of protein-reagent combinations to determine crystallization conditions. Coupled with an automated inspection station (e.g., AutoInspeX®, available from Fluidigm Corporation) multiple conditions are screened with a rapid pace and with minimal operator commitment.

Current methods evaluate the quality of macromolecular crystals through visual assessments made by a person skilled in crystal inspection. Crystals with well defined edges and otherwise of obvious crystalline appearance are typically judged of higher priority than crystals that have visual signs of defects within the lattice of the crystal. Although numerous designs have been advanced to provide for in situ x-ray diffraction of macromolecular crystals, problems are present in these designs. Thus, there is a need in the art for improved methods and systems related to diffraction-based crystallization analysis.

SUMMARY OF THE INVENTION

According to the present invention, techniques related to nanofluidic systems are provided. In particular, the invention provides an architecture including nanovolume crystallization chambers configured for use in x-ray crystallographic diffraction analysis systems. More particularly, the present method and system provides for a low volume crystallization chamber with reduced x-ray scattering suitable for in-situ crystallography. Merely by way of example, the nanofluidic methods and systems described herein have been applied to a chip geometry that supports reduced crystal sizes and features carbon-based elastomers in layers through which the x-ray beam passes. Although the techniques for nanofluidic systems are applied to x-ray diffraction analysis of macromolecular crystals, it would be recognized that the invention has a much broader range of applicability.

According to an embodiment of the present invention, an integrated fluidic circuit is provided. The integrated fluidic circuit includes a substrate including a support surface and a bonding surface opposing the support surface. The integrated fluidic circuit also includes a flow layer coupled to the bonding surface of the substrate and including a flow material characterized by a first thickness. The flow layer defines a plurality of reaction chambers having a height less than the first thickness. The integrated fluidic circuit further includes a control layer coupled to the bonding surface of the substrate and defining a plurality of control structures. The control layer includes a first layer of a first material characterized by a first x-ray scattering cross-section. The control layer also includes a second layer of a second material characterized by a second x-ray scattering cross-section less than the first x-ray scattering cross-section. The second layer is adjacent the first layer.

According to another embodiment of the present invention, an integrated microfluidic circuit for use in an x-ray diffraction analysis system is provided. The integrated microfluidic circuit includes a substrate. A normal to the substrate defines an x-ray beam path. The integrated microfluidic circuit also includes a flow layer coupled to the substrate and characterized by a first material having a first thickness measured along the x-ray beam path. The flow layer defines a plurality of reaction chambers characterized by a height measured along the x-ray beam path less than the first thickness and a plurality of valves in fluid connection with the plurality of reaction chambers. The plurality of reaction chambers are configured to receive a flow of one or more fluids. The integrated microfluidic circuit further includes a control layer coupled to the flow layer and characterized by a second thickness measured along the x-ray beam path. The control layer defines a plurality of control lines configured to actuate the plurality of valves and comprises a second material having a modulus of elasticity greater than a modulus of elasticity of the first material.

According to a specific embodiment of the present invention, a method of analyzing one or more crystals in an integrated fluidic circuit having a microchamber disposed in a flow layer and a control layer adjacent the flow layer is provided. The method includes dispensing a sample into a sample port in fluid communication with the microchamber and transferring the sample through the flow layer to the microchamber. The method also includes dispensing a reagent into a reagent port in fluid communication with the microchamber and mixing the sample and the reagent in the microchamber. The method further includes forming the one or more crystals in the microchamber and irradiating the one or more crystals in the microchamber with an analysis beam. The analysis beam passes through the one or more crystals in the microchamber present in the flow layer and through the control layer. The method additionally includes detecting the analysis beam.

According to another specific embodiment of the present invention, an integrated fluidic circuit is provided. The integrated fluidic circuit includes a substrate layer and a first structure coupled to the substrate layer and including a plurality of channels. The first structure is configured to provide for flow of one or more materials through the plurality of channels. The integrated fluidic circuit also includes a second structure coupled to the substrate layer and including a plurality of control channels configured to receive an actuation pressure. The integrated fluidic circuit is characterized by a thickness of less than 1.5 mm.

Numerous benefits are achieved using the present invention over conventional techniques. For example, an embodiment according to the present invention provides a reduction in the size of the crystallization chamber in comparison to conventional devices. Additionally, embodiments of the present invention provide for faster access to diffraction data than available using conventional crystallization techniques. Furthermore, some embodiments utilize reduced quantities of samples and reagents since determination of structure can be performed from minute quantities of material and diffraction data can be obtained in situ from most or all of the crystals present in a crystallization screen. Moreover, the diffraction quality of crystals can be measured before handling or cryoprotection. In a particular embodiment, diffraction data can be used to make decisions on which crystals are suitable for further analysis rather than visual assessment. Depending upon the embodiment, one or more of these benefits may exist. These and other benefits have been described throughout the present specification and more particularly below.

Various additional objects, features and advantages of the present invention can be more fully appreciated with reference to the detailed description and accompanying drawings that follow.

BRIEF DESCRIPTION OF THE DRAWINGS

FIG. 11A is a simplified schematic diagram of a device for supporting one or more sections of an integrated fluidic circuit according to an embodiment of the present invention;

FIG. 11B is a simplified schematic diagram of the device of FIG. 11A at liquid nitrogen temperature; and FIG. 11C is a simplified schematic diagram of the device of FIG. 11A at room temperature.

DETAILED DESCRIPTION OF SPECIFIC EMBODIMENTS

Figure 1:
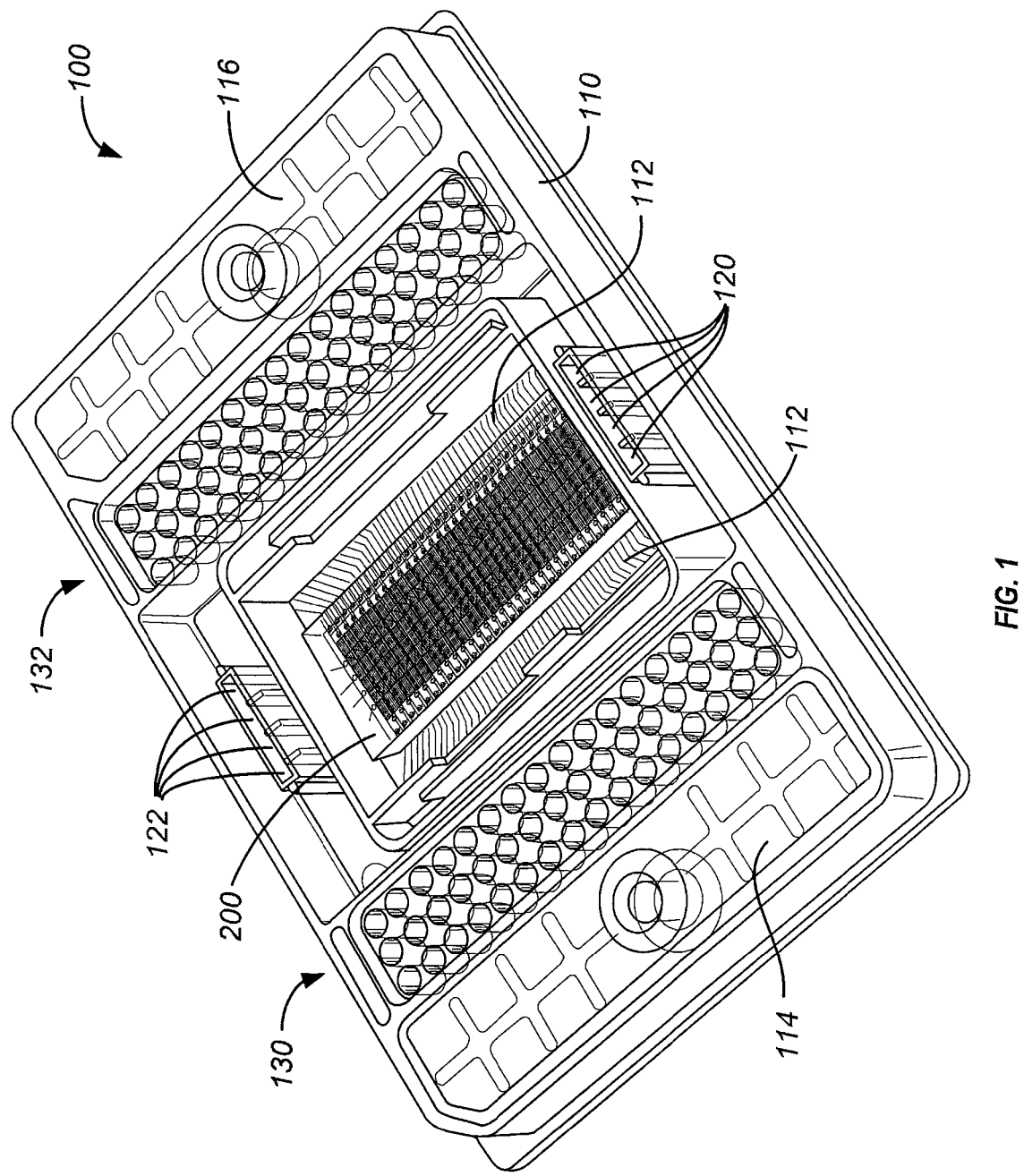
FIG. 1 is a simplified perspective illustration of a microfluidic chip including an integrated fluidic circuit (IFC) bonded to a carrier.

Microfluidic crystallization chips that have been used in or proposed for use in crystallography studies include those described in WO/05056813 and WO/04104228. Embodiments of the present invention use such microfluidic screening systems to obtain x-ray diffraction data from many or all crystallization experiments in a particular microfluidic device (chip or biochip). Diffraction data obtained from such a device allows one to determine which experiments contain useful crystals on the basis of the quality of diffraction data rather than judgments of visual quality. Additionally, embodiments of the present invention use a microfluidic screening apparatus to collect data sufficient to determine the structure of the molecules from which the crystals are formed. In some embodiments, x-ray diffraction data is obtained from the crystals without the need for removal of the crystals from the screening chip. Thus, embodiments of the present invention provide devices and systems for the rapid attainment of crystallographic data from a variety of screening chips, thereby accelerating the discovery of new macromolecular structures. One of ordinary skill in the art would recognize many variations, modifications, and alternatives.

Embodiments of the present invention provide a crystallization chip with the required architecture and material properties to obtain crystals and enable the measurement of in situ x-ray diffraction data from the crystals without unnecessary interference with the x-ray beam from the chip materials. Reducing interference with the x-ray beam comes from reducing the electron density of the (non-crystal) material through which the x-ray beam passes. These desired features are obtained through the use of low volume crystallization wells formed in a matrix that minimizes the amount of non-carbon based elastomer within the diffraction path of the chip.

A further aspect of the invention is a nanovolume crystallization chamber configured to restrict the size of the crystal grown in the crystallization chamber. In a further aspect, the crystallization chamber is configured to provide a minimum of space between walls of the chamber through which the x-ray beam passes. In an embodiment of the invention, the walls of the chamber through which the x-ray beam passes include a carbon-based elastomer. In embodiment utilizing carbon-based elastomers, it is preferred that the carbon based elastomer has sufficient mechanical strength to provide chip integrity while minimizing the thickness of the chamber walls. The in situ x-ray chip can be configured as a multilayered device having the same material in all layers. The chip can also be comprised of layers formed from different materials. Microfluidic device construction from a variety of materials, including elastomeric materials, has been described in U.S. Pat. Nos. 6,408,878, 6,793,753, and 7,195,670, the disclosures of which are hereby incorporated by reference. Valves as described herein, which are actuated through the interaction between materials and pressures in the flow and control layers, can be considered to lie in the flow layer and to be actuated by application of pressure to control lines present in the control layer. Thus, by pressurizing the control lines in the control layer, a flexible membrane is actuated or deflected to close off a portion of one or more flow channels formed in the flow layer. Since the flow in the flow layer is modified by closing of the valve, the valve is referred to as being present in the flow layer. One of skill in the art will appreciate that definitions of a valve may not include the actuating members, but may relate to the region of the flow layer into which the deflected membrane passes upon actuation. Additional discussion related to valves and actuation thereof is provided in relation to FIGS. 7A-7H of U.S. Pat. No. 7,195,670.

When constructing a multilayer in situ x-ray chip from dissimilar materials, it is necessary to ensure adequate bonding between the various layers. A particular embodiment of the invention provides a multilayer integrated fluidic circuit or chip with an elastomeric central layer comprised of a first elastomer, such as polydimethylsiloxane (PDMS). The chip in this embodiment further includes planar peripheral layers that sandwich the central layer. The planar peripheral layers comprise a carbon-based elastomer, such as a urethane elastomer, poly olefin films, or a non-carbon-based elastomer/carbon-based elastomer composite layer.

In some embodiments, chip geometry is selected to limit crystal growth and limit the quantity of solvent in the path length of the crystallization chamber. The spacing between peripheral layers is also selected to provide structural integrity for the crystallization chamber while limiting crystal growth so that the macromolecular crystal (e.g., a protein crystal) lies adjacent to the crystallization chamber walls. A crystal grown against the walls of the chamber acts to exclude chamber solvent and thereby minimizes solvent scattering effects. The thickness of the intermediate layer has sufficient thickness to impart volume in the chamber, give structural integrity to the chip, and provide the necessary plumbing and control for operation of the chip.

FIG. 1 is a simplified perspective illustration of an integrated fluidic circuit attached to a carrier. As illustrated in FIG. 1, the chip 100, includes a carrier 110, which may be made from materials providing suitable mechanical support for the various elements of the carrier. An integrated fluidic circuit 200 is mounted on the chip. As an example, the carrier is made using a plastic or other suitable material. The outer portion of the carrier has the same footprint as a standard 384-well microplate and enables stand-alone valve operation. As described below, there are eight sample input ports or inlets, with four sample input ports 120 located one side of the carrier and four additional sample input ports 122 located on the opposite side of the carrier.

The carrier 110 also includes 96 reagent input ports 130 and 132. A integrated fluidic circuit 200 is mounted on the carrier 100 in fluidic communication with the various sample and reagent input ports. As described in additional detail below, the integrated fluidic circuit 200 provides a number of reaction chambers configured to support crystallization processes, such as macromolecular crystallization. As illustrated in FIG. 1, microfluidic channels 112 connect the various fluid sources to the reaction chambers on the integrated fluidic circuit 200.

Pressure is applied to accumulators 114 and 116 in order to open and close valves connecting the fluid sources to the reaction chambers. Although 8 sample input ports and 96 reagent input ports are shown in the embodiment of the present invention illustrated in FIG. 1, this is not required by the present invention. Other embodiments utilize a different number of samples and reagents depending on the particular application. In applications in which reagents are not utilized, the reagent input ports and the accumulator, or portions thereof, may not be used.

Figure 2A:
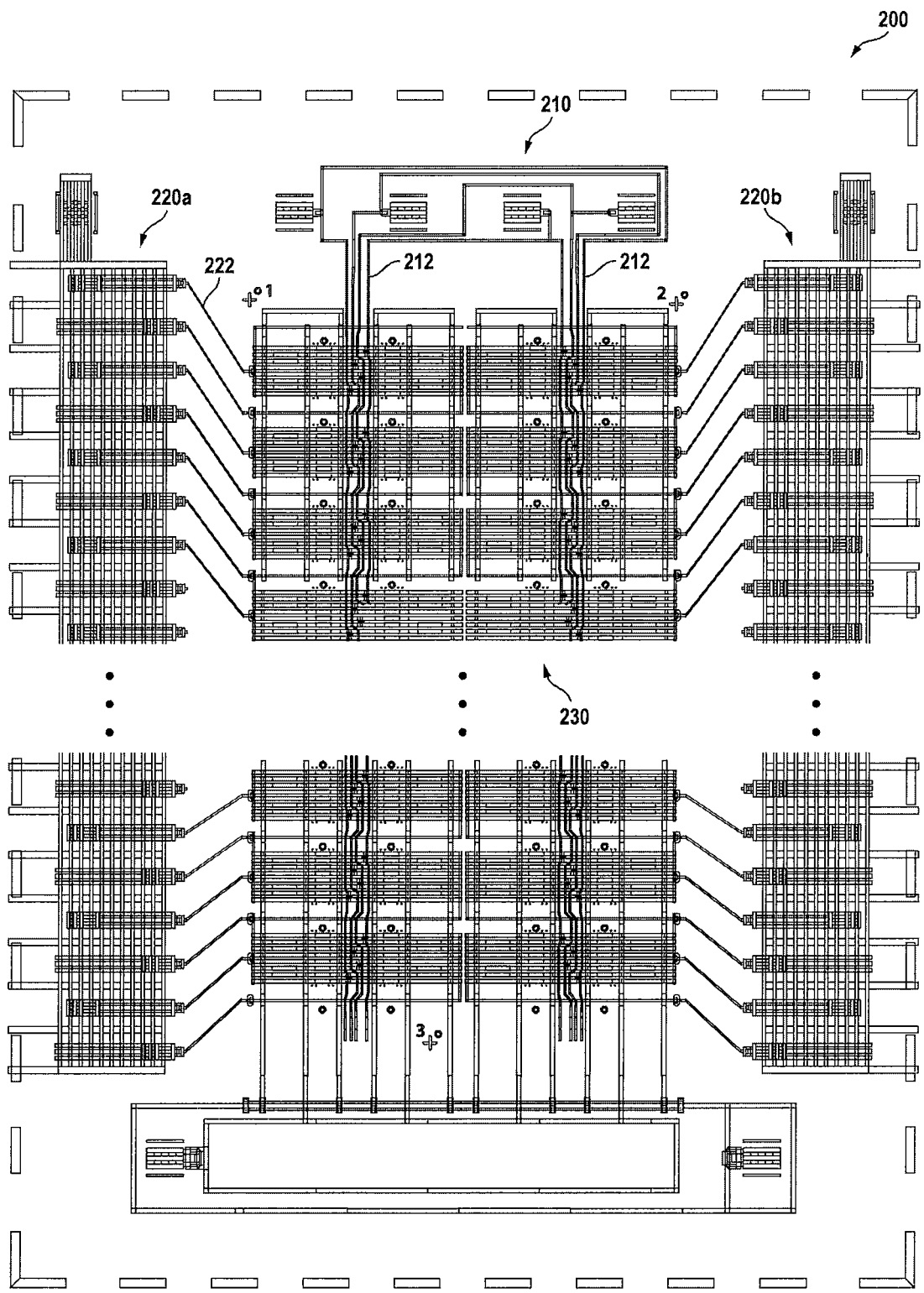
FIG. 2A is a simplified schematic diagram of an integrated fluidic circuit according to an embodiment of the present invention.

FIG. 2A is a simplified schematic diagram of an integrated fluidic circuit according to an embodiment of the present invention. The integrated fluidic circuit may also be referred to as an integrated microfluidic circuit. The integrated fluidic circuit 200 illustrated in FIG. 2A includes four sample ports 210 that are adapted to receive up to four samples that will be distributed throughout the integrated fluidic circuit. Sample fluid lines 212 are provide that run from the sample ports 210 to the various reaction chambers 230 (e.g., sample chambers and reagent chambers) as described in relation to FIG. 2B. Although four sample ports are illustrated in FIG. 2A, this particular number is not required by embodiments of the present invention. In other embodiments, the number is varied depending on the particular application, for example, eight sample ports, or the like.

The integrated fluidic circuit also includes a number (e.g., 96) reagent ports 220a and 220b. Reagents provided to the reagent ports are able to flow through reagent fluid lines 222 to the various reaction chambers 230. The ellipsis in the middle of FIG. 2A illustrate that only a portion of the reagent ports are shown in this particular figure. Additionally, other numbers of reagent ports are utilized in other embodiments, as appropriate to the particular application. Utilizing the ports, fluid lines, and control lines (not shown for purposes of clarity), combinations of the various samples are reagents are provided at varying concentrations in the various reaction chambers present on the integrated fluidic circuit. Additional description of integrated fluidic circuits is provided in commonly assigned U.S. Pat. No. 6,408,878, issued on Jun. 25, 2002, and entitled "Microfabricated elastomeric valve and pump systems," the disclosure of which is hereby incorporated by reference in its entirety.

Figure 2B:
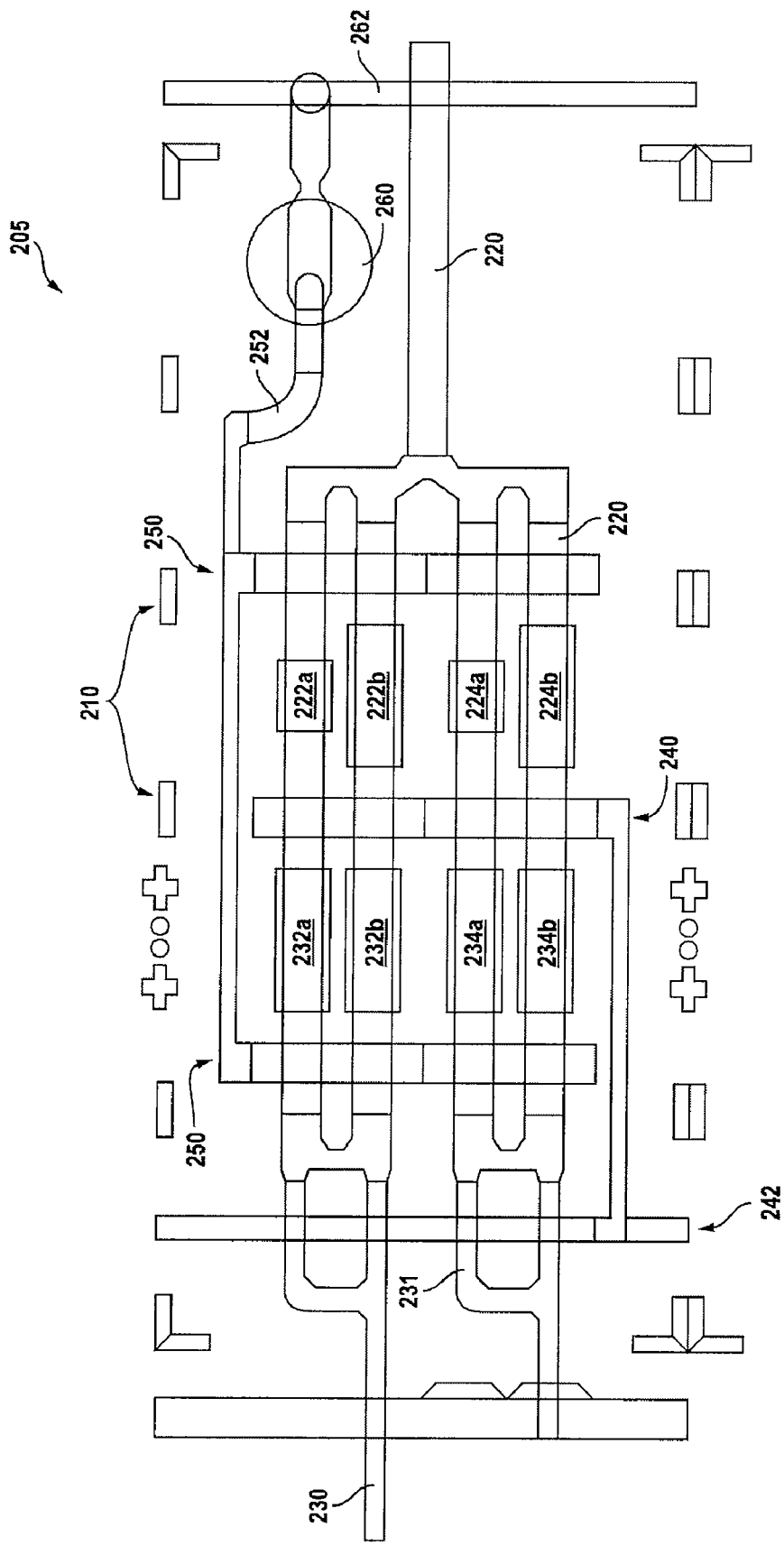
FIG. 2B is a simplified schematic diagram of a section of the integrated fluidic circuit illustrated including check valve structures in FIG. 2A.

FIG. 2B is a simplified schematic diagram of a section 205 of the integrated fluidic circuit 200 illustrated in FIG. 2A. FIG. 2B illustrates a set of reagent chambers and sample chambers connected by microfluidic channels and valves as described more fully below. The dashed lines 210 represent a section 205 of the integrated fluidic chip 200 suitable for excision in preparation for x-ray diffraction analysis. Although excision of section 205 is not required by embodiments of the present invention, in some applications including low temperature x-ray diffraction analysis, the sections of the integrated fluidic chip are excised and mounted in suitable testing mounts prior to analysis. Punching, stamping, or other methods are utilized according to embodiments of the present invention in order to excise the section 205 from the chip 200. One of ordinary skill in the art would recognize many variations, modifications, and alternatives.

Referring to FIG. 2B, reagent microfluidic channels 220 provide for flow of reagent to reagent chambers 222a, 222b, 224a, and 224b. As illustrated in FIG. 2B, reagent chambers 222a and 224a are characterized by a larger chamber volume than reagent chambers 222b and 224b. Thus, the amount of reagent contained in the two sets of reagent chambers will differ as appropriate to the particular application. Merely by way of example, reagent chambers 222a and 224a have a volume of 10 nl and reagent chambers 222b and 224b have a volume of 5 nl in a particular embodiment. As described below, other chamber volumes are included within the scope of the present invention and these particular values are provided merely as an example. In the embodiment illustrated in FIG. 2B, the same reagent is provided to reagent chambers 222a, 222b, 224a, and 224b via the microfluidic channels 220, with differing amounts of reagents per chamber as described above. In other embodiments, the microfluidic channels are arranged to provide for different reagents in the various reagent chambers.

Samples are provided to sample chambers 232a, 232b, 234a, and 234b via microfluidic channels 230 and 231, which are in fluid communication with sample sources (not shown). As illustrated in FIG. 2B, two different samples are provided to the sample chambers, with a first sample provided to sample chambers 232a and 232b and a second sample provided to sample chambers 234a and 234b. The sample chambers are characterized by a particular volume, for example 10 nl as appropriate to the particular application.

Isolation or interface valves 240 are provided between the sample chambers and reagent chambers. Upon initial loading of the samples and reagents, the interface valves 240 are closed by application of pressure from an external pressure source (not shown) supplied to valve line 242. After loading of the sample and reagents, containment valves 250 are closed by application of pressure from another external source (not shown) supplied to valve lines 252, isolating the samples and reagents in the corresponding chambers. In order to provide for free interface diffusion of the samples and reagents, interface valves 240 are opened, allowing for mixing of the samples are reagents in opposing chambers. Modification of the pressure in valve lines 242 is typically utilized to open the previously closed interface valves. Crystal formation is facilitated as a result of diffusion, although this could be enhanced by the use of thermocycling or other suitable processes. While this embodiment of the invention facilitates crystallization through free-interface diffusion, one of ordinary skill in the art would recognize that integrated fluidic circuits could be designed to facilitate crystallization through other methods.

Embodiments of the present invention provide for diffraction capable screening chips (biochips, microfluidic chips, and the like) in which both the integrated fluidic circuit and the carrier are designed for crystallization and data collection. Thus, data can be collected directly from the chip with reduced or no manual handling of the chip. In other embodiments, sections of the chip are removed for x-ray testing as described more fully throughout the present specification. In some embodiments, cryoprotection and oscillation data collection are provided for either the entire chip or sections of the chip. One of ordinary skill in the art would recognize many variations, modifications, and alternatives.

Referring to FIG. 2B, check valve 260 is provided in the section 205. As discussed previously, in some applications, collection of x-ray diffraction data from crystals grown in integrated fluidic circuits can be conducted by removing sections of the integrated fluidic circuit and placing them directly in the X-ray beam. Embodiments of the present invention provide for the dashed lines 210 as guides during the excision process in preparation for data collection. During excision, one or more of the control lines (e.g., valve lines 240 and 242) are typically ruptured during excision of the chip section, which may result in loss of valve function. Merely by way of example, if the valve line 242 providing pressure to close the containment valves 250 leading to the reagent chambers is severed, the containment valves may partially or fully open, resulting in loss of fluid from the reagent chambers. Air may enter the reagent and/or sample chambers via the control lines and result in uncontrolled dehydration of the materials in the sample and reagent chambers, for example, a macromolecular crystal.

Embodiments of the present invention provide check valve 260, which, among other functions, provides for isolation of the chip section 205 after excision procedures. Thus, embodiments of the present invention provide for isolation of the individual experiments (sample/reagent combinations) while retaining valve functionality. The check valve 260 illustrated herein is a normally closed check valve that can maintain a closed state with essentially no back pressure. The normally closed check valve can be readily produced by multilayer soft lithographic techniques and may retain effective functioning through many thousands of opening and closing cycles without failure.

The check valve 260 is incorporated in the design of the integrated fluidic chip at a position on the containment control line 262. During operation, the check valve 260 is actuated before excision of the chip section 205. This check valve will hold pressure in the containment valves within a chip section even after it has been excised from the main chip body. Additional description of check valves suitable for use in embodiments of the present invention is found in commonly assigned International Application No. PCT/US2007/080489 (International Publication No. WO 2008/043046 A2), filed on Oct. 24, 2007, and entitled "Microfluidic check valves," the disclosure of which is hereby incorporated by reference in its entirety for all purposes.

Figure 3A:
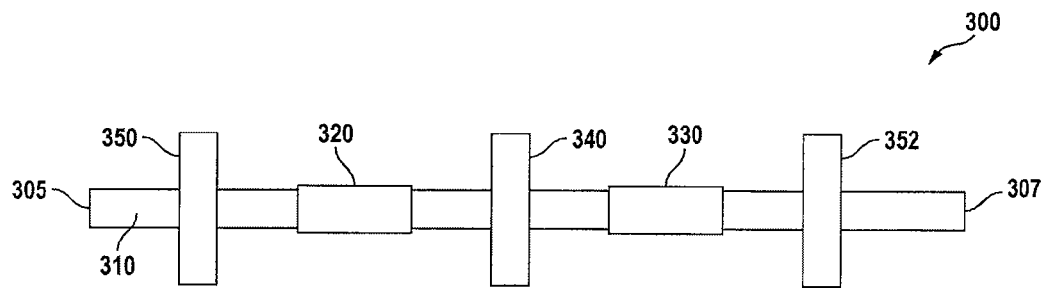
FIG. 3A is a simplified top view illustration of a unit cell of an integrated fluidic circuit architecture according to an embodiment of the present invention.

FIG. 3A is a simplified top view illustration of an integrated fluidic circuit architecture according to an embodiment of the present invention. In some embodiments, the integrated fluidic circuit architecture is referred to as a microfluidic chip architecture. The top view illustration shown in FIG. 3A is representative of a portion of the chip section 205 illustrated in FIG. 2B. In a particular example, the volume of the sample chamber is 10 nl, although this is not required by the present invention. In some embodiments, the volume of the sample chamber determines, in part, the width, length, and height of the sample chamber, which, as described below, may be related by ratios.

Referring to FIG. 3A and the top view illustration of a unit cell suitable for in situ x-ray diffraction studies, the unit cell 300 includes a flow channel 310 fed from each end (305 and 307) with two adjacent chambers, a sample chamber 320 and a reagent chamber 330, in fluidic communication through the flow channel. The reagent chamber and the sample chamber can be fluidically isolated from each other through the closure of an interface valve 340. The flow channel, in this example, is formed in a gas permeable elastomer. Additional discussion of the materials utilized in fabricating devices according to embodiments of the present invention are described more fully below.

A crystallization experiment is performed in a specific embodiment by first actuating the interface valve 340 to fluidically isolate the sample chamber and the reagent chamber. Reagent solution is introduced into the flow channel 310 through channel end 307. Sample solution is introduced into the flow channel 310 through channel end 305. Under pressure, the sample and reagent solutions displace the residual gas in the flow channel that, in turn, escapes through the gas permeable channel walls. The reagent solution, entering through 307 fills the reagent chamber 330 and the flow channel up to the closed interface valve 340. The sample solution, entering through 305, fills the sample chamber 320 and the flow channel up to the closed interface valve 340. The containment valves, 350 and 352, are then closed after the chambers have been filled in order to retain the reagent solution and the sample solution that have been loaded into their respective chambers. Interface valve 340 is then opened and the reagent chamber and the sample chamber are placed in fluidic communication. Diffusion occurs between the reagent chamber and the sample chamber. As the structural layers become thinner, the layers become more permeable, enabling lower vapor pressure materials to escape. Thus, embodiments of the present invention utilize materials, e.g. polyurethanes, that are less gas permeable, enabling a similar gas permeability using a thinner structural layer. Thus, in some embodiments, although the thickness of the control layer is reduced in comparison to conventional designs, the permeability of the control layer is similar to that characterizing conventional designs. As a result, the rates of evaporation associated with integrated fluidic circuits described herein are comparable to conventional structures despite the thin nature of the circuit. Of course, variation in the evaporation rates may also be provided as appropriate to the particular application. One of ordinary skill in the art would recognize many variations, modifications, and alternatives.

In a particular embodiment, the width of the sample chamber 320 and the reagent chamber 330 measured in the plane of FIG. 3A perpendicular to the flow channel 310 is 200 µm. The height of the sample chamber 320 and the reagent chamber 330 measured perpendicular to the plane of FIG. 3A and the flow channel 310 is 40 µm and the height of the flow channel measured along the same direction is 20 µm. In the embodiment illustrated in FIG. 3A, the thickness of the integrated microfluidic circuit is 230 µm, the thickness of the PDMS in the beam path is 35 µm, the chamber volume is 10 nl and the maximum crystal dimension in the beam path is 40 µm. As described more fully throughout the present specification, the particular geometric features are selected to provide for reduced x-ray scattering and suitable crystal size.

Figure 3B:
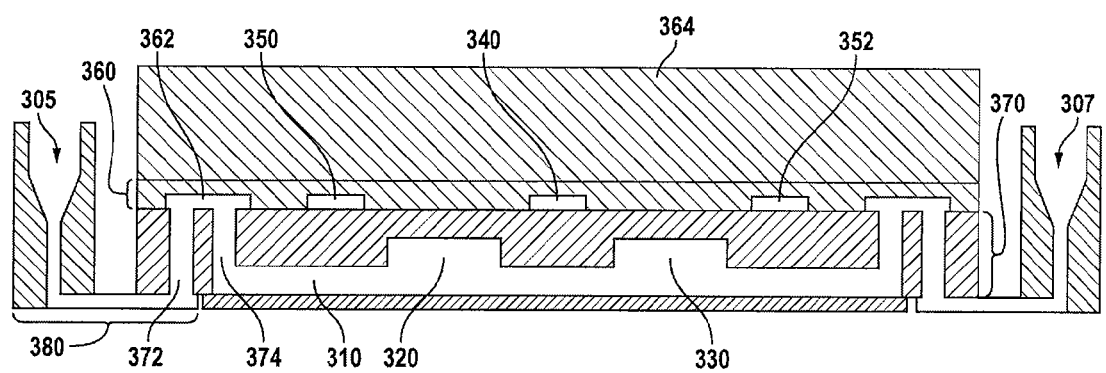
FIG. 3B is a simplified side view illustration of an integrated fluidic circuit architecture according to an embodiment of the present invention.

FIG. 3B is a simplified side view illustration of am integrated fluidic circuit architecture according to an embodiment of the present invention. The illustration provided in FIG. 3B shows the basic chip architecture for an embodiment of the present invention. The reference numbers utilized in FIG. 3A are utilized in FIG. 3B for purposes of clarity. An intermediate layer 370 containing the flow channel and the reagent and sample chambers (flow layer) is prepared using soft lithographic techniques. The flow channels are sealed by adhering a peripheral backing material (not shown) to the flow layer by placing an elastomeric layer or film backing.

The fluidic connections between the flow channels and the chambers and between the adjacent chambers can be interrupted by the deflection of a wall of the flow channel into and against the opposite wall of the channel. This is accomplished by a layer of control channels (control layer) in the peripheral layer 360 (also referred to as a flow layer) adjacent to the flow layer. The control layer 360, in this embodiment, is also prepared by photolithographic techniques. The thickness of one or more portions of the control layer 360 is decreased by embodiments of the present invention in comparison with conventional control layers. The control layer 360 contains channels (control channels) that can be pressurized with gas or liquid. If a portion of the control channel overlays a portion of a flow channel in the adjacent layer (340, 350, and 352), the pressurization of the fluid (gas or liquid) in the control channel causes the deflection of the wall of the flow channel to fluidically isolate the adjacent portion of the flow channel 310. The deflection of the wall is enhanced if the area of the control channel overlaying the flow channel is widened as compared to the width of the control channel. This overlayed area forms the valves of the microfluidic device. As illustrated in FIG. 3B, layer 364 is a sacrificial layer that is used during manufacturing of the control layer and then can be removed to provide the thin control layer 360 shown in FIG. 3B. In some embodiments, layer 364 remains on top of control layer 360 during use. One of ordinary skill in the art would recognize many variations, modifications, and alternatives.

In the embodiment illustrated in FIG. 3B, there is a control channel for actuating the containment valves 350 and 352 that isolate the sample and reagent chambers 320 and 330, respectively, from the flow channels inlets 305 and 307 and a separate control channel for actuating the interface valves 340 that isolate the fluidic communication between the reagent chamber and the sample chamber. The integrated fluidic circuit (IFC) is generally mounted on a carrier 380 that facilitates handling of the IFC and provides the interface for filling samples and reagents into the IFC. An exemplary carrier is illustrated, for example, in FIG. 1.

As illustrated in FIG. 3B, one or more combinations of vias 372 and 374 are punched through the intermediate flow layer of the IFC. An interconnecting channel in the control layer connects the flow path through vias 372 and 374. In this manner, the chip can be attached to a carrier on the periphery of the chip so that it is connected with one or more wells on the carrier. As described more fully throughout the present specification, filling the well(s) with reagent solution or sample solution and applying pressure to the well(s) drives the solution(s) into the flow channel(s) in the chip through via 372, interconnecting channel 362, and via 374.

Figure 3C:
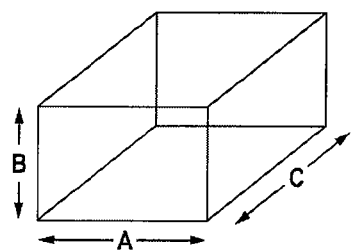
FIG. 3C is a simplified illustration of chamber geometry according to an embodiment of the present invention.

FIG. 3C is a simplified illustration of chamber geometry according to an embodiment of the present invention. In FIG. 3C, the directions aligned with the A and C axes are illustrated as lying in the plane of the chip section 205 illustrated in FIG. 2B. The direction aligned with the X axis is orthogonal to the A and C directions. Although not a requirement, the ratio of A:C should be from about 1:7 to about 7:1. A more preferred range is from about 1:5 to about 5:1. A ratio of A:C of from about 1:3 to about 3:1 is most preferred. Certain embodiments of the invention will benefit from an A:C ratio of from about 0.8:1 to about 1.2:1, more preferred from about 0.85:1 to about 1.15:1, more preferred from about 0.9:1 to about 1.1:1, more preferred from about 0.95:1 to about 1.05:1. The most preferred ratio of A:C in this embodiment is about 1:1.

Assuming that the B axis is aligned with the x-ray beam path, then the preferred ratio of B:C is about 1:2 or greater, more preferred about 1:5 or greater, more preferred is about 1:10 or greater, more preferred is about 1:25 or greater, more preferred is about 1:50 or greater. A ratio of B:C of greater than 1:50 is well suited for obtaining high quality x-ray diffraction data. In some embodiments, the B:C ratio can be in the range of from about 1:2 to about 1:5, from about 1:5 to about 1:10, from about 1:10 to about 1:20. Specific embodiments of B:C ratio of about 1:10, about 1:15, about 1:20, about 1:25, about 1:30, about 1:35, about 1:40, about 1:45, and about 1:50 Ratios of B:C of about 1:75 or great, 1:100 or greater, or about 1:200 or greater can be advantageous.

The various aspect ratios provided herein are not limited by the examples discussed, but are meant to include additional ratios as well. In some embodiments, a generally flat aspect ratio chamber is provided, reducing the path analysis beams travel as they propagate through the chamber, thereby reducing the background scattering resulting from interaction between electromagnetic radiation present in the analysis beam and the material surrounding the chamber. As described more fully throughout the present specification, the low aspect ratio characteristic of the reaction chambers limits the height of the crystals (e.g., macromolecular, protein, or other crystals) grown in the reaction chambers. Additionally, for crystals that fill the chamber vertically, little to no solvent is encountered along the direction of propagation of the analysis beam as the beam passes through the crystal, thereby resulting in additional reductions in background scatter. Thus, the various specific aspect ratios included in this specification are provided merely by way of example and do not limit the scope of embodiments of the present invention.

In general, larger B:C ratios will facilitate collection of larger oscillation ranges and a more complete range of scattering angles. For chips where larger numbers of experiments are desired and a less complete range of diffraction data is acceptable, the A:B ratio can be higher and A:C can become more rectilinear.

Figure 4:
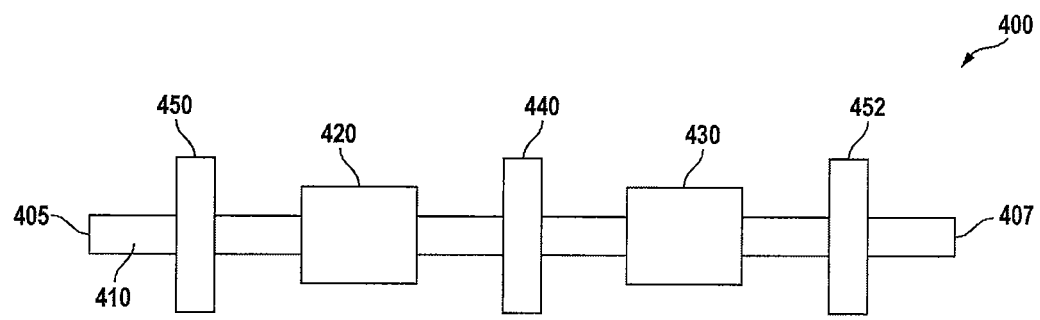
FIG. 4 is a simplified top view illustration of a unit cell of an integrated fluidic circuit architecture according to another embodiment of the present invention.

FIG. 4 is a simplified top view illustration of unit cell of an integrated fluidic circuit architecture according to another embodiment of the present invention. The unit cell 400 illustrated in FIG. 4 shares some common features with the unit cell 300 illustrated in FIG. 3 and includes a flow channel 410 fed from each end (405 and 407) with two adjacent chambers, a sample chamber 420 and a reagent chamber 430, in fluidic communication through the flow channel. The reagent chamber and the sample chamber can be fluidically isolated from each other through the closure of an interface valve 440. The flow channel, in this example, is formed in a gas permeable elastomer. Additional discussion of the materials utilized in fabricating devices according to embodiments of the present invention are described more fully below.

A crystallization experiment is performed in a specific embodiment by first actuating the interface valve 440 to fluidically isolate the sample chamber and the reagent chamber. Reagent solution is introduced into the flow channel 410 through channel end 407. Sample solution is introduced into the flow channel 410 through channel end 405. Under pressure, the sample and reagent solutions displace the residual gas in the flow channel that, in turn, escapes through the gas permeable channel walls. The reagent solution, entering through 407 fills the reagent chamber 430 and the flow channel up to the closed interface valve 440. The sample solution, entering through 405, fills the sample chamber 420 and the flow channel up to the closed interface valve 440. The containment valves, 450 and 452, are then closed after the chambers have been filled in order to retain the reagent solution and the sample solution that have been loaded into their respective chambers. Interface valve 440 is then opened and the reagent chamber and the sample chamber are placed in fluidic communication. Diffusion occurs between the reagent chamber and the sample chamber.

In a particular embodiment, the width of the sample chamber 420 and the reagent chamber 430 measured in the plane of FIG. 3A perpendicular to the flow channel 410 is 100 μm. The height of the sample chamber 420 and the reagent chamber 430 measured perpendicular to the plane of FIG. 3A and the flow channel 410 is 20 μm and the height of the flow channel measured along the same direction is 10 μm. As described more fully throughout the present specification, the particular geometric features are selected to provide for reduced x-ray scattering and suitable crystal size. The small sample and reagent chamber volumes provide for low protein consumption in some embodiments, for example, a total protein consumption per integrated fluidic circuit of less than 2 μl. In the embodiment illustrated in FIG. 4, the thickness of the integrated microfluidic circuit is 140 μm, the thickness of the PDMS in the beam path is 25 μm, the chamber volume is 2 nl and the maximum crystal dimension in the beam path is 20 μm.

Figure 5:
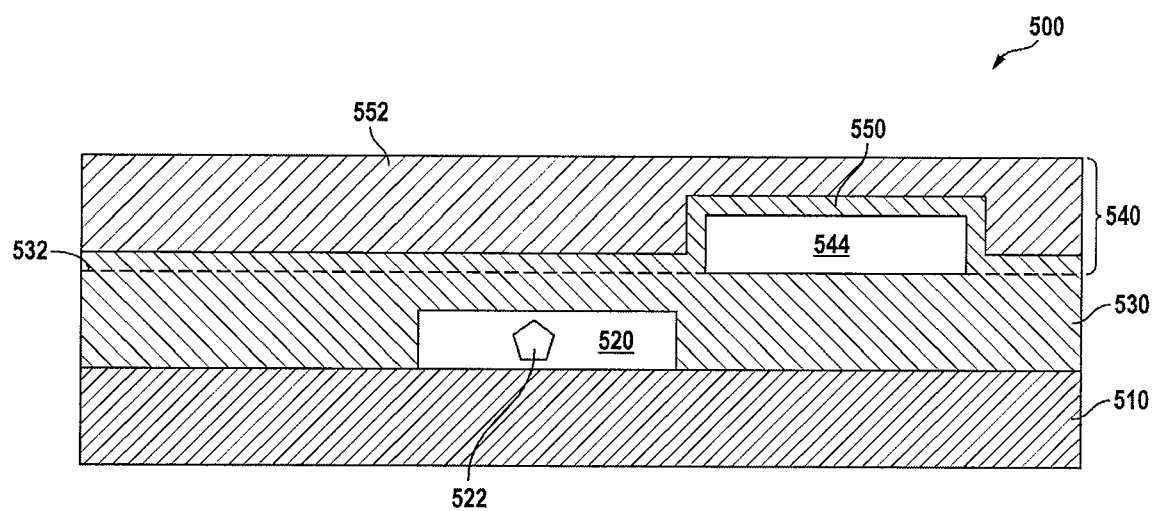
FIG. 5 is a simplified cross-section of an integrated fluidic circuit architecture according to an embodiment of the present invention.

FIG. 5 is a simplified cross-section of an integrated fluidic circuit architecture according to an embodiment of the present invention. As illustrated in FIG. 5, the architecture of an embodiment of a composite microfluidic crystallization screening chip 500 is shown that was prepared using multi-layer soft lithographic techniques. The bottom peripheral layer 510 in this embodiment is a backing layer that is an extruded cyclic olefin polymer. A reaction chamber 520 including crystal 522 is illustrated in middle intermediate layer 530. In some embodiments, this middle intermediate layer 530 is referred to as a flow layer and is made of PDMS. The thickness of layer 530 is selected to provide for a short x-ray diffraction path and a chamber height that limits the crystal size. The upper peripheral layer 540, also referred to as the control layer, is a laminate of PDMS 550 and urethane 552. The control layer 540 includes the control channel 544. During assembly, the top side of the control layer 540 is bonded to a thick layer of PDMS doped with A32 adhesive (not shown) to allow for handling. The bottom side of the control layer is bonded to the PDMS of layer 530 at interface 532.

In the embodiment illustrated in FIG. 5, the laminate or composite control layer 540 includes a PDMS layer 550 that is thinner than the height of the control lines 544. In some embodiments, the height of the control line 544 ranges from about 5 μm to about 50 μm and the thickness of layer 550 (e.g., PDMS) ranges from about 10 nm to about 10 μm, and the thickness of layer 552 (e.g., urethane or a urethane blend) ranges from about 10 μm to about 100 μm. In a particular embodiment, the height of the control line 544 is approximately 20 μm, the thickness of layer 550 (e.g., PDMS) is approximately 0.5 μm, and the thickness of layer 552 (e.g., urethane or a urethane blend) is approximately 50 μm. Thus, in a particular embodiment, the amount of the PDMS in the beam path is equal to the difference between the thickness of flow layer 530 and the height of the reaction chamber 520 (i.e., the portion of layer 530 above the reaction chamber) summed together with the thickness of layer 550 when made from PDMS. The remaining material in the beam path above the crystal (e.g., urethane) is characterized by a lower x-ray scattering cross-section than that associated with PDMS, resulting in a reduction in the background x-ray scattering caused by the materials of the integrated microfluidic circuit. In embodiments in which layer 540 is formed using a single material (e.g., layer 550 and 552 are both made using one or more urethanes), the thickness of PDMS in the beam path is equal to the portion of layer 530 above the reaction chamber. Thus, in contrast with conventional microfluidic devices, embodiments of the present invention provide devices suitable for in situ x-ray analysis with reduced background scattering.

According to embodiments of the present invention, materials are utilizes for fabrication of the integrated fluidic circuit that are clear (e.g., defined in terms of lack of inclusions) so that the integrated fluidic circuit and carrier can be inserted into a beam path of an x-ray diffraction analysis system. Although discussion of x-ray diffraction analysis systems is provided herein, embodiments of the present invention are not limited to such systems. Other systems utilizing electromagnetic radiation (e.g., fluorescence) are included within the scope of the present invention and materials and structures described herein provide for reductions in scattering of radiation passing through the integrated fluidic circuit for a variety of wavelengths. Thus, in a particular embodiment, materials that provide a reduction in background scattering for optical radiation are utilized to provide a thin circuit with sufficient mechanical rigidity for fluorescence applications. Additionally, the material has to have sufficient mechanical strength to support other portions of the circuit while providing a short transit path for x-rays. Processing parameters of materials utilized herein include a reasonable curing schedule, the ability to spin coat the material, and suitable for standard hazardous material handling requirements.

Chamber volumes for reaction chamber 520 can range from about 0.5 to about 200 nL. Preferred ranges of chamber volumes may depend on the particular application selected for the chip. A preferred range is from about 0.5 nL to about 150 nL, more preferred from about 0.5 nL to about 125 nL, more preferred from about 0.5 nL to about 100 nL. Particular purpose chips may be designed with volumes of from about 0.5 nL to about 5 nL, from about 2 nL to about 12 nL, from about 10 to about 15 nL, from about 40 nL to about 60 nL, and from about 85 nL to about 120 nL. Specific embodiments include 0.7 nL, 2 nL, 5 nL, 10 nL, 15 nL, 25 nL, 50 nL, and 100 nL.

Embodiments of the present invention provide for reduced thickness of the upper peripheral layer 540. Preferably, the peripheral layer thickness is from about 10 µm to about 350 µm, more preferably, from about 10 µm to about 250 µm, more preferably from about 10 µm to about 200 µm, more preferably from about 10 µm to about 150 µm. It is preferred that the peripheral layer thickness is about 250 µm or less, more preferred about 225 µm or less, more preferred about 200 µm or less, more preferred about 175 µm or less, more preferred about 150 µm or less, more preferred about 125 µm or less, more preferred about 100 µm or less, more preferred 75 µm or less, more preferred 50 µm or less. In alternate embodiments, peripheral layer thicknesses may be about 15 µm, about 20 µm, about 25 µm, about 30 µm, about 35 µm, about 45 µm, about 50 µm, about 60 µm, about 75 µm, about 85 µm, or about 100 µm. The peripheral layer, when prepared as a laminate structure, typically minimizes the thickness of materials, such as PDMS, that cause x-ray background scatter.

Crystallization chamber thickness, as defined by the thickness of the intermediate layer 530, can be from about 7 µm to about 250 µm. In an embodiment, the crystal chamber thickness is from about 7 µm to about 200 µm. In a preferred embodiment, the crystal chamber thickness is from about 7 µm to about 100 µm. In a more preferred embodiment, the chamber thickness is about 75 µm or less, more preferred is about 60 µm or less, more preferred is about 50 µm or less, more preferred is about 40 µm or less, still more preferred is about 30 µm or less. Within these ranges, the choice of thickness is a balance between obtaining suitably large crystals to provide good diffraction data while selecting minimal capacity to physically limit the growth of the crystal. Preferred crystallization chamber thicknesses can be about 7 µm, or the following ranges of thickness: about 8 µm to about 10 µm; about 10 µm to about 15 µm; about 15 µm to about 20 µm; about 20 µm to about 35 µm; about 35 µm to about 50 µm; about 50 µm to about 60 µm, about 60 µm to about 70 µm, about 70 µm to about 80 µm, about 80 µm to about 90 µm, and about 90 µm to about 100 µm.

The ratio of the thickness of the mold features (i.e., the height of the control lines) in the control layer to the thickness of the control layer is a predetermined value in some embodiments of the present invention. Additionally, the ratio of the thickness of the mold features (i.e., the height of the reaction chambers) in the flow layer to the thickness of the flow layer is the same or a different predetermined value in some embodiments of the present invention. For example, the thickness of the flow layer is less than ten times the height of the mold features (e.g. photoresist) used to fabricate the control layer. Thus, the total thickness to feature thickness is less than ten in some embodiments. In a particular embodiment, the total thickness of the flow layer is less than five times, four times, three times, or two times the height of the reaction chambers. In another particular embodiment, the total thickness of the control layer is less than five times, four times, three times, or two times the height of the control lines.

The uncured peripheral layer elastomer should have a viscosity suitable for formation of thin films either through extrusion, casting or through spin-layering. Preferred materials include PET, polycarbonate, urethane or many other carbon plastics with similar density and hardness. In an embodiment, the control layer is fabricated using a urethane blend of WC-595 (a high hardness Shore A urethane) mixed with WC-781 (a high hardness Shore D urethane with extended working time). This particular urethane blend provides a suitable combination of hardness, elasticity, and a processing window suitable for in situ x-ray diffraction analysis. Other urethane blends are utilized in other embodiments as appropriate to the particular application. In some embodiments, the material utilized in the layer 540 has a modulus of elasticity greater than a modulus of elasticity of the material utilized in the layer 550. As an example, the modulus of elasticity (or other measure of the stiffness of a material) of urethane or a urethane blend is greater than the modulus of elasticity of PDMS. The increased stiffness of the materials in the control layer provides for reductions in thickness while maintaining mechanical rigidity.

Bonding of dissimilar elastomeric layers is facilitated through techniques such as surface oxidation, application of an adhesive intermediary layer, co-curing of adjacent layers, and combinations of these methods. Manipulation of the peripheral layer(s) may be accomplished by temporarily adhering a peripheral layer to a bulk polymer layer. The bulk polymer layer may be composed of a variety of elastomeric materials. Adhesion between the bulk polymer layer and the peripheral layer can be enhanced through the use of polymeric dopants in one or both layers. In one embodiment, an amine-bearing polydimethyl siloxane derivative is doped in the bulk uncured polymer matrix. Curing of the doped layer allows functional groups of the dopant to remain at the interfacing surface. The interaction of these functional groups with the polymer chains at the surface of the adjacent layer enhances adhesion of the layers. Alternately, both of the adjacent layers may contain dopant. Optimal adhesion between layers will depend on the particular polymer of the bulk layer, the dopant added to the bulk layer, the quantity of dopant in the bulk polymer layer(s), and the curing process to which the bulk layers and the laminate layer is subjected. The adhesion should be reversible to allow for the manipulation of the peripheral layer in the chip manufacturing process and then the release of the layer once it has been attached to the central layer.

In an embodiment, the thickness of the integrated fluidic circuit is 220 µm, the chamber volume is 100 nl, and the maximum crystal dimension in the x-ray diffraction analysis beam is 100 µm. In another embodiment, the thickness of the integrated fluidic circuit is 250 µm. In yet another embodiment, the thickness of the integrated fluidic circuit is 180 µm, the chamber volume is 10 nl, and the maximum crystal dimension in the x-ray diffraction analysis beam is 40 µm. In an alternative embodiment, the thickness of the integrated fluidic circuit is 140 µm, the chamber volume is 2 nl, and the maximum crystal dimension in the x-ray diffraction analysis beam is 20 µm. In other embodiments, these particular values are modified as appropriate to the particular application. It should be noted that the thin designs for the integrated fluidic circuit described herein can be compared to designs in which the thickness of the integrated fluidic circuit is 5 mm, the chamber volume is 0.75 nl, and the maximum crystal dimension in the x-ray diffraction analysis beam is 10 µm.

Because of the geometry of the integrated fluidic circuit, embodiments of the present invention provide for in situ x-ray diffraction analysis of crystals or other features formed in the reaction chambers provided on the integrated fluidic circuit. In a conventional technique, crystals grown in a reaction chamber are removed from the reaction chamber and mounted in a mounting loop in preparation for x-ray analysis. According to embodiments of the present invention, the integrated fluidic circuit is mounted in the x-ray diffraction analysis stage along with the carrier or alone. Since the height of the reaction chamber is small, the scattering of the x-rays along the x-ray beam path is reduced, enabling in situ analysis to be performed. As described throughout the present specification, the materials, geometry, and the like of the integrated fluidic chip are selected to provide conditions suitable for in situ x-ray diffraction analysis.

It should be noted that embodiments of the present invention provide functionality not available using conventional techniques. For example, embodiments described herein provide for formation of protein or other crystal structures in closed reaction chambers in which the concentrations of materials, such as reactants and samples, are controlled via activation of valves provided in the control layer. Thus, in contrast with microtiter plates or other techniques in which fluids are distributed to enclosed volumes, embodiments of the present invention provide control over reaction conditions while still providing for in situ analysis of crystal features. Because of the complexity of the integrated fluidic circuit, including the flow and control layers, and the interaction therebetween, the inventors have developed methods and systems that include materials for both complex material control and in situ analysis.

Figure 6:
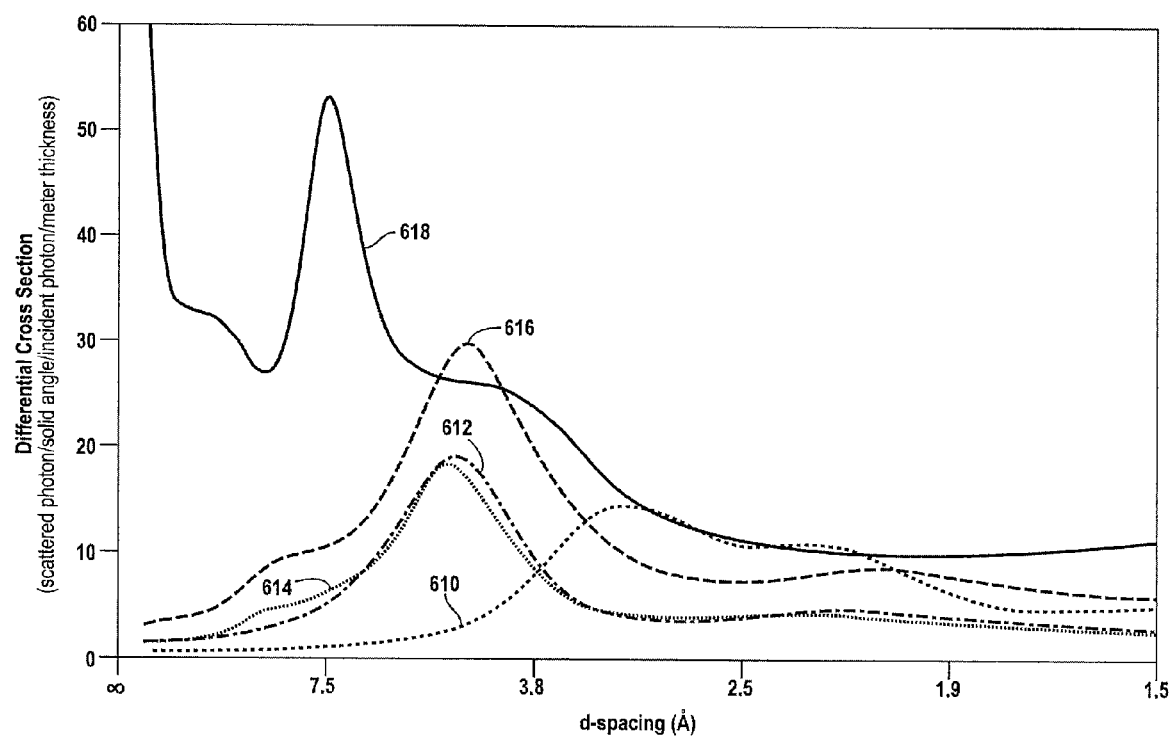
FIG. 6 is a simplified plot of differential cross-section as a function of lattice spacing according to an embodiment of the present invention.

FIG. 6 is a simplified plot of differential cross-section as a function of lattice spacing according to an embodiment of the present invention. The differential cross-section (also referred to as a scattering cross-section or an x-ray scattering cross-section), which is measured in scattered photons per solid angle per incident photon per meter of thickness is plotted as a function of lattice spacing for a variety of different materials. As discussed below, the x-ray scattering cross-section or properties of carriers and microfluidic device materials were determined as part of the design process. In this specification, x-ray scattering cross-section is used as a term to describe the amount of x-ray scattering generated per unit thickness of material. For x-ray scattering experiments, it is desirable for the amount of x-ray scattering from materials used to hold samples to be minimized. The scattering cross-section of water (610), paratone-N oil (612), a first plastic (Clear-Flex-50™ urethane plastic available from Smooth-On of Easton, Pa.)) (614), a second plastic (TASK 9™ urethane available from Smooth-On of Easton, Pa.)) (616) and PDMS (618) are illustrated as examples. Paratone-n oil is a commonly used cryoprotectant used as a carrier for macromolecular crystals in x-ray diffraction experiments. The scattering properties of these materials, and other materials including a 25% glycerol solution, were measured in relation to their use as carrier and chip materials. Embodiments of the present invention utilize materials characterized by a difference in scattering cross-sections. For example, in a particular embodiment, the material present on top of the reaction chamber produces less than 5% of the background scatter. In an alternative embodiment, the material present on top of the reaction chamber produces less than 95% of the background scatter. In other embodiments, the amount of background scatter ranges between about 5% and about 95%, for example, 10%, 15%, 20%, 25%, 30%, 40%, 50%, 60%, 70%, 80% or 90%.

According to embodiments of the present invention, an in situ crystallization/diffraction device will preferably have x-ray scattering properties similar to properties associated with a conventional, low throughput, method. As illustrated in FIG. 6, paratone-n oil shows maximal diffraction at a d-spacing of 5 Å. Similar results were shown with the second plastic. PDMS showed strong diffraction at 3.5 Å and above. The strong background scattering pattern of PDMS indicates that for an in situ crystallization/diffraction device, the amount of PDMS, or other strongly scattering material, should be reduced or minimized along the x-ray beam path. The other elastomeric materials, for example, the first and second plastic, demonstrate improved performance over PDMS and are characterized by similar properties to paratone-n oil per unit thickness of material.

In addition to reductions in scattering provided by the materials selected for the carrier and/or in situ crystallization/diffraction chip, embodiments of the present invention reduce the amount of solvent in the x-ray beam path. The inventors have determined that the solvent surrounding the crystal contributes to the background scattering associated with in situ x-ray diffraction analysis of crystals present in IFCs. Thus, embodiments of the present invention reduce the amount of solvent in the beam path, for example, by reducing the chamber volume. In a particular embodiment, the height of the reaction chamber, measured along the direction of the beam path, is reduced to reduce the chamber volume. In addition to reducing the scattering resulting from solvent in the beam path, the reduced chamber height tends to limit the crystal size and encourage the grown of spatially separated crystals.

The inventors have determined that a number of elastomeric materials are suitable for use in embodiments of the present invention. Allcock et al, in Contemporary Polymer Chemistry, 2nd Ed. describe elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

In an exemplary aspect of the present invention, the first material with higher background scattering will be an elastomeric polymer such as GE RTV 615 (formulation), a vinylsilane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This process uses cured layers that possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability. For materials in the path of the x-ray beam, reduced x-ray background scatter may be of paramount importance and thus materials such as carbon based elastomers are preferred in some embodiments. Mechanical rigidity and impermeability to water vapor are desired qualities and, therefore, the selection of chip materials is made with these and other properties in mind.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene

Pure polyisobutylene has no double bonds, but is crosslinked to use as an elastomer by including a small amount (about 1%) of isoprene in the polymerization. The isoprene monomers give pendant double bonds on the polyisobutylene backbone, which may then be vulcanized as above.

Poly(styrene-butadiene-styrene)

Poly(styrene-butadiene-styrene) is produced by living anionic polymerization (that is, there is no natural chain-terminating step in the reaction), so "live" polymer ends can exist in the cured polymer. Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes

Polyurethanes are produced from di-isocyanates (A-A) and di-alcohols or di-amines (B-B); since there are a large variety of di-isocyanates and dialcohols/amines, the number of different types of polyurethanes is huge. Urethanes such as WC-565, FASTFLEX C, LS-60, WC-781, all available from BJB Enterprises, Inc., Tustin, Calif., are suitable for practicing certain embodiments of the present invention. The A vs. B nature of the polymers makes them useful for heterogeneous multilayer soft lithography, as are the silicone polymers.

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

Cross Linking Agents

In addition to the use of the simple "pure" polymers discussed above, crosslinking agents may be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

Other Materials

In addition, polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical may also be used. The following is a non-exclusive list of elastomeric materials which may be utilized in connection with the present invention: polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytetrafluoroethylene (Teflon).

Dopants are utilized in some embodiments (e.g., amine dopants in PDMS) to provide a transfer substrate used during manufacturing. The dopants provide for tackiness during fabrication so that a temporary bond to urethane or other peripheral material layer can be formed to the transfer substrate. After fabrication, the temporary bond is broken, enabling for release of the urethane/doped PDMS interfacial bond. The inventors have determined that PDMS is not generally tacky enough to adhere to the urethane layer during fabrication processes. However, use of dopants with the PDMS provide tackiness suitable for a temporary bond. One of ordinary skill in the art would recognize many variations, modifications, and alternatives.

Embodiments of the present invention provide for new methods of construction and new structures based on the use of urethane materials (or other suitable materials) that are more mechanically stable, for a given thickness, than conventional materials, such as PDMS. In some embodiments, composite layers of PDMS and urethane are utilized to provide for adhesion along with mechanical stability. The use of polyurethane in the control layers provides for a thin integrated fluidic circuit that is mechanically stable, durable, foldable, and flexible. Thus, although some embodiments are described in relation to x-ray diffraction analysis, embodiments of the present invention are not limited to this particular application, but are also useful in additional applications.

According to embodiments of the present invention, the total thickness of the integrated fluidic circuit ranges from about 10 µm to about 1.5 mm. The total thickness may be about 1.5 mm, 1.0 mm, 750 µm, 500 µm, 250 µm, 200 µm, 150 µm, 125 µm, 100 µm, 90 µm, 80 µm, 70 µm, 600 µm, 500 µm, 25 µm, or 10 µm. Values within these ranges are also included in the scope of embodiments of the present invention.

In an exemplary method of fabricating a structure, amine dopants are incorporated into PDMS in order to provide a transfer wafer used during manufacturing. In an embodiment, the method includes forming a spin layer including a composite PDMS/urethane layer onto a substrate, forming a flow layer including an amine-doped PDMS layer coupled to the composite layer, and lifting off the combination of the spin layer and the flow layer. The method also includes bonding the PDMS/urethane layer to another portion of the structure, and peeling off the flow layer from the transfer wafer. As described above, the doping of the PDMS with amines provide a surface that adheres to the composite layer during fabrication processes and still is able to be removed after fabrication without damage to the composite layer.

Examples of polymer dopants include: aminopropyl terminated polydimethylsiloxanes with molecular weights of about 850-900, about 900-1000, about 3000, about 5000, about 25,000, and about 30,000, containing % amine functionality of about 3.2-3.8%, about 3.0-3.0%, about 1.0-1.2%, about 0.6-0.7%, about 0.11-0.12%, and about 0.08-0.09% respectively; N-ethylaminoisobutyl terminated polydimethylsiloxane; aminopropylmethylsiloxane-dimethylsiloxane copolymers; aminoethylaminopropylmethylsiloxane-dimethylsiloxane copolymers; aminoethylaminoisobutylmethylsoloxane-dimethylsiloxane copolymers; and aminoethylaminoisopropylmethoxysiloxane-dimethylsiloxane copolymers. The quantity of dopant in the bulk polymer can range from about 0.001% to about 15%. A preferred range is from about 0.25% to about 10%. More preferred is from about 1 to about 7%.

Figure 10:
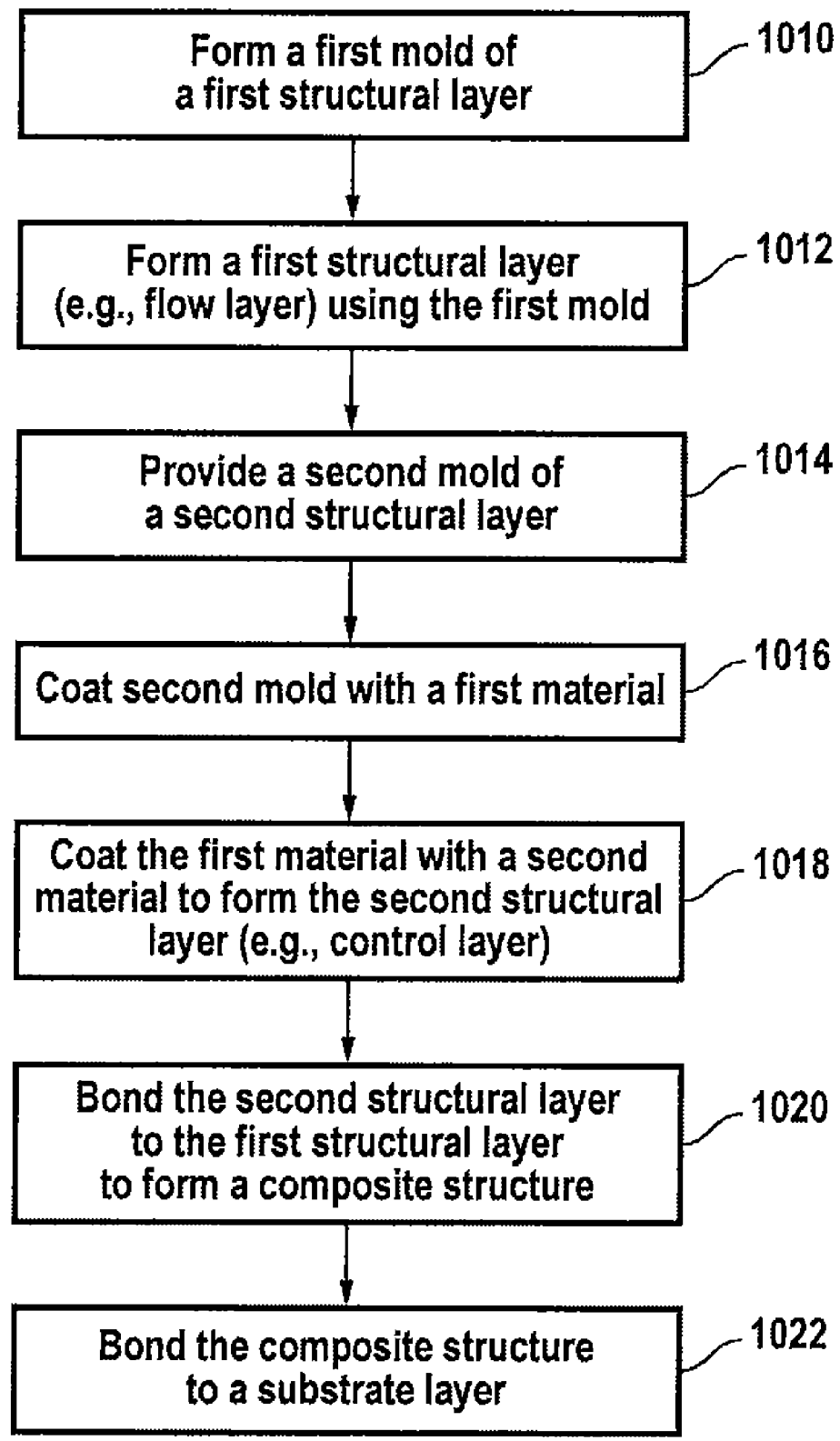
FIG. 10 is a simplified flowchart illustrating a method of fabricating an integrated fluidic circuit according to an embodiment of the present invention.

FIG. 10 is a simplified flowchart illustrating a method of fabricating an integrated fluidic circuit according to an embodiment of the present invention. Fabrication of the microfluidic devices in this embodiment of the present invention are prepared using multilayer soft lithographic techniques. A photoresist mold of a first structural layer (e.g., the intermediate flow layer) is formed (1010) and attached to a turntable and rotated at high speed. The first mold may be formed during the process illustrated in FIG. 10 or previously by the same or different party. An uncured elastomer resin is poured on the central point of the rotating mold and the elastomer resin is evenly distributed outward over the photoresist mold by the centripetal force acting on it (1012). Thus, a first structural layer is formed that is attached to the first mold. The mold may then be removed from the turntable and the resin is allowed to cure. The curing can be accelerated by raising the temperature of the mold/elastomer resin layer.

A second mold is formed for a separate structural (e.g., peripheral control) layer (1014). The second structural layer is formed by coating the second mold with a first material (1016). Then the first material is coated with a second material to thereby form the second structural layer (1018). In an embodiment, the first material is PDMS, which provides adhesion to the first structural layer including PDMS and the second material is a polyurethane material. Materials for the various layers are described in additional detail throughout the present specification. In an alternative embodiment, the first material and the second material are the same material, thus making step 1016 optional in this alternative embodiment. The first material and the second material are generally cured or undergo additional processing. The second structural layer is removed from the second mold and aligned over and bonded to the first structural layer (1020) to form a composite structure.

The composite structure is removed from the first mold and bonded to a substrate layer. In some applications, the substrate layer is adjacent to the first (e.g. flow) layer to seal the flow channels of the flow layer (1020). In one embodiment, channels (vias) are incorporated into the flow layer to allow reagent and sample solutions to enter the flow channels when routed through the adjacent peripheral control layer. As described above, vias facilitate the routing of fluids in a microfluidic device in a fashion that is analogous to manner in which through-plating of connections on a double-sided printed circuit board facilitate the routing of electrical connections.

It should be appreciated that the specific steps illustrated in FIG. 10 provide a particular method of fabricating an integrated fluidic circuit according to an embodiment of the present invention. Other sequences of steps may also be performed according to alternative embodiments. For example, alternative embodiments of the present invention may perform the steps outlined above in a different order. Moreover, the individual steps illustrated in FIG. 10 may include multiple sub-steps that may be performed in various sequences as appropriate to the individual step. Furthermore, additional steps may be added or removed depending on the particular applications. One of ordinary skill in the art would recognize many variations, modifications, and alternatives.

According to an embodiment of the present invention, a method of fabricating an integrated fluidic circuit is provided. The method includes providing a first mold of a first structural layer (e.g., a flow layer). The first mold may be fabricated using photoresist materials or other suitable mold materials. The method also includes forming the first structural layer using the first mold, generally performed by spinning an elastomeric material (e.g., PDMS) onto the mold. The method further includes providing a second mold of a second structural layer (e.g., a control layer). The second mold, which may be fabricated using photoresist materials, is coated with a first material (e.g., PDMS to provide a strong bond to the material in the first structural layer) and then a second material (e.g., polyurethane to provide mechanical rigidity and low electron density). The method additional includes bonding the second structural layer to the first structural layer to form a composite layer and bonding the composite layer to a substrate layer. The first and second structural layers are removed from their associated molds as appropriate during fabrication.

Fabrication of a particular 1.96 x-ray diffraction chip was accomplished by preparing the peripheral control layer by spinning a layer of elastomer resin having a 1:10:1 ratio of a trimethylsiloxy terminated PDMS resin to RTV 615A to RTV 615B resin on the control layer photoresist mold. The PDMS peripheral control layer was cured and a polyurethane resin was spun on top of the PDMS layer. The polyurethane layer was allowed to cure and bond to the underlying PDMS layer. This yielded a composite layer with a thickness of approximately 3 µm PDMS and approximately 100 µm of polyurethane. A removable adhesive pour layer was cast on top of the polyurethane surface of the control layer to facilitate removal of the control layer from the mold and to allow the manipulation of the thin control layer.

The intermediate flow layer was prepared by spinning 10:1 ratio of RTV 615A to RTV 615B PDMS resin over a photoresist mold that defined 100 µm wide flow channels of 10 µm height. The mold also defined sample and reagent chambers of 20 μm height with a total volume of 2 nL. Total thickness of this layer was approximately 23 μm. Following spinning, the mold and resin mixture layer was removed from the turntable and allowed to cure. Vias were laser-punched in the flow layer to facilitate liquid routing when the chip was mounted to a carrier similar to that described in US 2005/0214173A1. The peripheral control layer was removed from the mold. The PDMS surface of the peripheral control layer and the exposed upper surface of the intermediate flow layer while it was still attached to the flow layer mold were treated with plasma to oxidize the surface and promote the bonding of the layers once they were mated. Following plasma treatment, the control layer was aligned and adhered to the flow layer. The peripheral control layer/intermediate flow layer composite structure was peeled off of the flow layer mold and a 0.002" extruded cyclo-olefin film was applied as a peripheral layer to the intermediate flow layer to seal the flow channels and chambers defined by the flow layer mold.

Alternate embodiments of chip architecture include the use of "push-up" valves for the control layer rather than the push-down valves illustrated in FIG. 5. As will be evident to one of skill in the art, the placement of the flexible membranes that define the valve structures is dependent on the particular application. In a particular "push down" embodiment, the lower layer is the control layer and is generally a thin PDMS layer with a carbon-based polymer laminated onto it. The flow layer defining the chambers remains the intermediate layer and the peripheral layer that is the backing layer is applied to the top of the intermediate layer. In yet other alternative embodiments, compound structures are utilized in which the flow layers are sandwiched around a control layer. In this case, multiple substrate layers abutting the flow layers may be utilized on opposing sides of the compound structure. Thus, although FIG. 5 illustrates a particular embodiment of the present invention in which the layers are arranged as substrate/flow/control, this is not required by the present invention. Other designs including substrate/control/flow, substrate/flow/control/flow/substrate, control/flow/substrate, variations not utilizing substrates, and the like, are included within the scope of embodiments of the present invention.

An in situ x-ray diffraction chip was constructed with 96 pairs of 2 nL chambers based on the design in FIG. 3A using the architecture illustrated in FIG. 3B and FIG. 5. The architecture of the chip, in this example, was configured so that once the interface valves are closed to fluidically isolate the reagent chambers from the sample chambers, the sample chambers remain in fluidic communication with a single channel inlet until the containment valves are actuated. The chambers on the opposite side of the interface valve (reagent chambers) each have individual inlets that are fluidically isolated from the reagent chambers upon actuation of the containment valves. Using this chip architecture, a single sample was loaded into the chip along with 96 separate reagent solutions. This is referred to as a 1×96 or 1.96 architecture. Once the containment valves are actuated to seal the chambers, the interface valves are opened to allow diffusion to occur between the 96 isolated reagent chambers and the 96 isolated sample chambers that each contain identical sample solutions. After an appropriate period of time elapsed, the sample chambers are evaluated for the presence of crystals and x-ray diffraction spectra are collected. Although a 1.96 architecture was utilized in this exemplary embodiment, this is not required by embodiments of the present invention. Other applications include 4.96 architectures, 8.96 architectures, and the like. One of ordinary skill in the art would recognize many variations, modifications, and alternatives.

Figure 7:
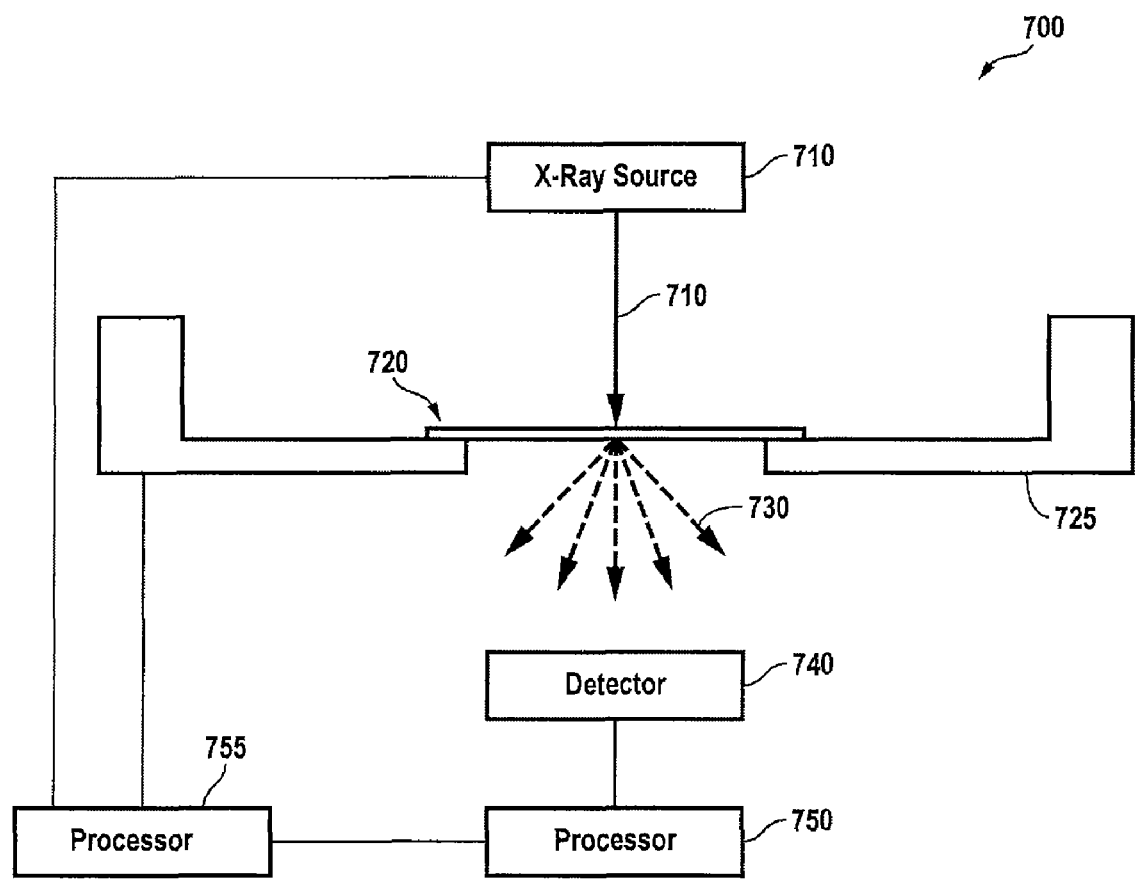
FIG. 7 is a simplified schematic diagram of an in situ x-ray analysis system according to an embodiment of the present invention.

FIG. 7 is a simplified schematic diagram of an in situ x-ray analysis system 700 according to an embodiment of the present invention. As illustrated in FIG. 7, a source of x-rays 710, for example, beamline 12.3.1 at the Advanced Light Source, Lawrence Berkeley National Laboratory, Berkeley, Calif. generates a beam of x-rays 715 incident on the integrated fluidic circuit 720. The integrated fluidic circuit 720 may be a full biochip or a section thereof removed after a process flow. The integrated fluidic circuit 720 is mounted in carrier 725 in FIG. 7 although this is not required by embodiments of the present invention. The mount for the integrated fluidic circuit/carrier combination may be adjustable in multiple dimensions and configured for testing at room temperature or other suitable (e.g., liquid nitrogen) temperatures. One of skill in the art will appreciate that the stage utilized for supporting the integrated fluidic circuit/carrier combination may be modified for data collection as appropriate to the particular application.

Diffracted x-rays 730 are collected by detector 740, which is coupled to processor 750. The processor 750 is configured to perform analytical functions associated with the x-ray diffraction analysis process. Controller 755 is coupled to the processor 750, the mount for the integrated fluidic circuit/carrier combination and the x-ray source in the embodiment illustrated in FIG. 7. Utilizing the system 700 illustrated in FIG. 7, x-ray diffraction data can be collected while crystals or other features present in the reaction chambers are present in the reaction chambers. In some embodiments, no additional handling of the crystals is required. Using embodiments of the present invention, it is possible to distinguish proteins or other macromolecules from salts, DNA, detergents, compound crystals, and the like.

Figure 8:
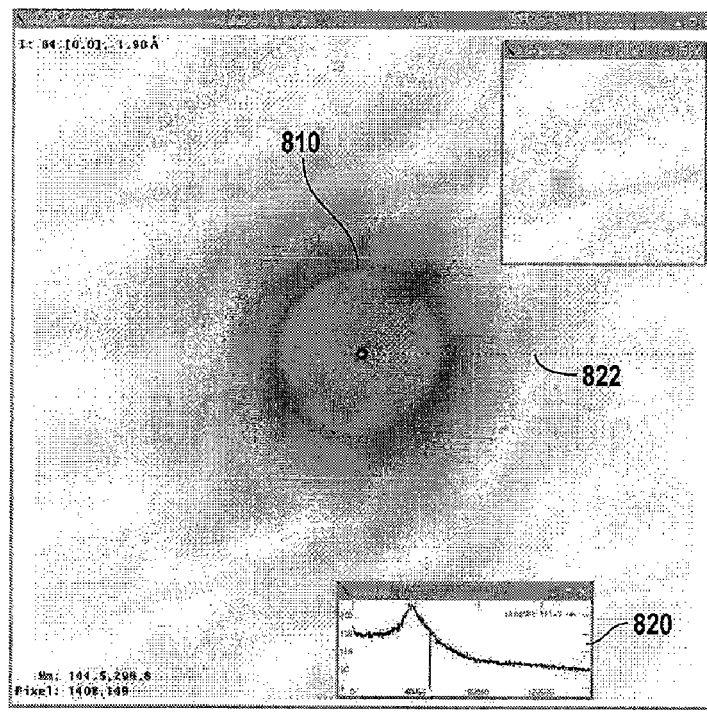
FIG. 8 illustrates x-ray diffraction data collected using an in situ x-ray diffraction system similar to that illustrated in FIG. 7.

FIG. 8 illustrates x-ray diffraction data collected using an in situ x-ray diffraction system similar to that illustrated in FIG. 7. The x-ray diffraction data illustrated in FIG. 8 was collected from crystals grown from a chip with a maximal chamber thickness of 40 μm and a 10 nL volume. The crystals are of the protein, thaumatin. The crystals were grown by loading a solution of 25 mg/mL thaumatin (Sigma-Aldrich Company, St. Louis) in water into a 10 nL chamber and loading an isolated adjacent 10 nL chamber with a solution containing 0.6M Na tartrate, pH 7.0. After the loading of the reagent solution and the protein solution, the isolation valves were closed and the interface valve was opened. The reagent was permitted to interact with the protein solution by free interface diffusion resulting in crystallization of the protein. Prior to data collection, a section of the chip was removed using an elliptical punch (Technical Innovations, Inc.) and mounted in an arterial clamp soldered to a standard magnetic base for mounting crystallization loops. Data was collected at room temperature at beamline 12.3.1 at the Advanced Light Source, Lawrence Berkeley National Laboratory, Berkeley, Calif.

Referring to FIG. 8, the beam location is illustrated at the center of the x-ray diffraction pattern. Without limiting embodiments of the present invention, the inventors believe that the ring 810 is associated with background scatter from the material used to fabricate the integrated fluidic circuit. In order to reduce this background scatter, embodiments of the present invention utilize materials characterized by a reduced number of electrons in the beam path of the x-ray beam in comparison with conventional materials. Thus, materials having a low atomic number (Z), or a low density, for example, carbon-based elastomers, are utilized in some embodiments to replace silicon-based elastomers. Thus, embodiments of the present invention reduce the background scattering from the materials, resulting in an increased signal associated with scattering from the crystals present in the reaction chamber or microchamber.

Referring once again to FIG. 8, some of the background scatter present in the x-ray diffraction data is associated with the solvent present in the reaction chamber or microchamber. As discussed previously, embodiments of the present invention reduce the amount of solvent in the beam path, for example, by reducing the chamber volume. The reduction in chamber volume reduces the scattering resulting from solvent in the beam path.

The inset 820 in the lower portion of FIG. 8 is a cross-section of the x-ray diffraction data taken along the dashed line 822. The diffraction signal climbs towards the position of the ring 810 and then falls off toward the edge of the data image. According to embodiments of the present invention, reductions in background due to low electron content materials and reduced amounts of solvent provide x-ray diffraction data with reduced a background signal and an increase in the relative intensity of data associated with crystallographic features of the sample. Thus, utilizing embodiments of the present invention, in situ analysis is possible, resulting in systems that are capable of automatically analyzing some or all of the crystals present in an integrated fluidic circuit in an automated fashion.

Figure 9:
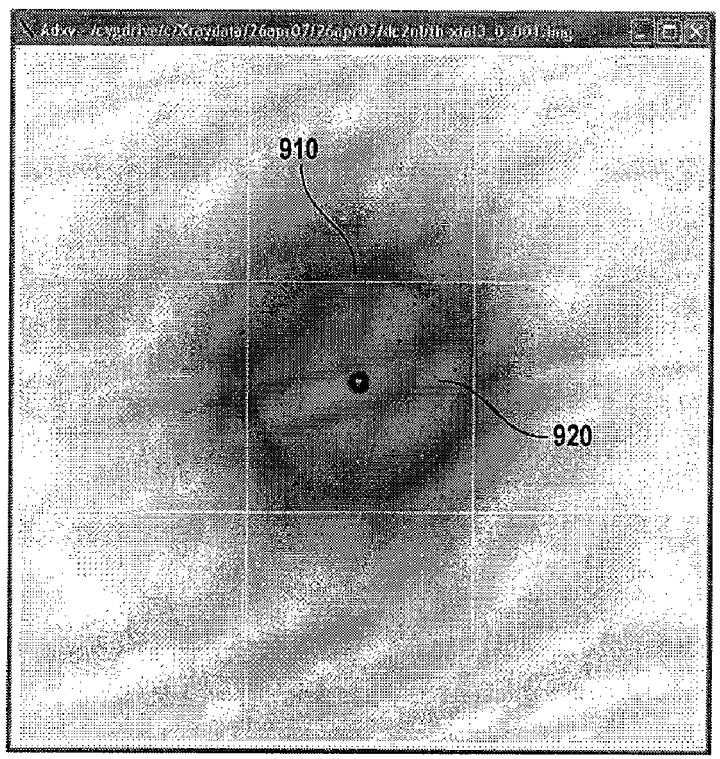
FIG. 9 illustrates additional x-ray diffraction data collected using an in situ x-ray diffraction system similar to that illustrated in FIG. 7.

FIG. 9 illustrates additional x-ray diffraction data collected using an in situ x-ray diffraction system similar to that illustrated in FIG. 7. The x-ray diffraction data illustrated in FIG. 9 was collected from crystals grown from a chip with maximal well thickness of 20 μm and a 2 nL volume. The crystals are of the protein, thaumatin. The crystals were grown by loading a solution of 25 mg/mL thaumatin (Sigma-Aldrich Company, St. Louis) in water into a 2 nL chamber and loading an isolated adjacent 2 nL chamber with a solution containing 0.6M Na tartrate, pH 7.0. After the loading of the reagent solution and the protein solution, the isolation valves were closed and the interface valve was opened. The reagent was permitted to interact with the protein solution by free interface diffusion resulting in crystallization of the protein. Prior to data collection, a section of the chip was removed using an elliptical punch (Technical Innovations, Inc) and mounted in an arterial clamp soldered to a standard magnetic base for mounting crystallization loops. Before the section of chip was removed, glycerol was introduced into the crystal chamber to act as a cryoprotectant solution. Data was collected at 100K beamline 12.3.1 at the Advanced Light Source, Lawrence Berkeley National Laboratory, Berkeley, Calif.

As illustrated in FIG. 9, the beam location is illustrated at the center of the x-ray diffraction pattern. Without limiting embodiments of the present invention, the inventors believe that the outer ring 910 is associated with background scatter from the material used to fabricate the integrated fluidic circuit. Additionally, the inventors believe the inner ring 920 is associated with background scatter due to the solvent present in the reaction chamber.

Diffraction patterns in both FIGS. 8 and 9 show diffraction peaks associated with the crystal structure analyzed using the x-ray diffraction setup. In FIG. 8, these diffraction peaks are aligned along generally horizontal axes, whereas in FIG. 9, the diffraction peaks are aligned axes tilted at approximately 45°.

FIG. 11A is a simplified schematic diagram of a device for supporting one or more sections of an integrated fluidic circuit according to an embodiment of the present invention. According to embodiments of the present invention, methods and systems are provided for supporting one or more sections of an integrated fluidic circuit during in situ crystallography analysis. In an embodiment, the device illustrated in FIGS. 11A-C is utilized to hold the section(s) of the integrated fluidic device or chip in a fixed location at the beamline during x-ray diffraction data. Integrated fluidic circuits as described throughout the present specification are suitable for support in the device illustrated in FIG. 11A.

One method for supporting a chip is to mount the entire chip and carrier in an X-Y stage at the beamline. This enables collection of x-ray diffraction data at ambient temperature. However, in many cases, it is necessary to collect data from crystals maintained at cryogenic temperatures to reduce the destructive effects of radiation damage. In this case, mounting the entire chip and carrier presents some technical issues since the entire chip would need to be cooled in most applications. Cooling of the entire chip and carrier would consume enormous quantities of liquid nitrogen and would require significant engineering of hardware components to enable this option.

An alternative method involves the removal of sections of the chip, and mounting those sections in an appropriate holder that can be used with tools developed for maintaining single crystals in loops at cryogenic temperatures. Additional discussion of removing sections of the integrated fluidic circuit are provided throughout the present specification, for example, with reference to FIG. 2B. Once sections of IFCs have been excised, they can be held in several manners, including in a crocodile clip, an arterial clip attached to a magnetic base, or more favorably, a copper crystal loop mounting pin with a slot cut into it. Embodiments of the present invention utilize the copper pin method since it enables the use of existing tools for cryogenic data collection. However, the inventors have determined that a significant problem is present related to the use of these copper pins, available from Hampton Research of Aliso Viejo, Calif. Once a chip has been sectioned, the chip section needs to be positioned in the slot in the pin. After positioning, the copper pin must be crimped with a pair of pliers to ensure that the section is held tight.

Thus, embodiments of the present invention provide a new device and method for mounting chip sections at low temperatures that takes advantage of materials characterized by differential coefficients of thermal expansion to cause reversible temperature-dependent mechanical changes. As illustrated in FIG. 11A, the device 1100 is made from two materials with very different thermal expansion coefficients (e.g., copper and steel). The device 1100 includes two flaps 1110a and 1110b, with each flap including a material 1116a and 1116b with a higher coefficient of thermal expansion (e.g., copper) on the inside and a material 1114a and 1114b with a lower coefficient of thermal expansion (e.g., steel) on the outside.

The section of the chip 1120 is placed between the two flaps 1110a and 1110b. Upon introduction into liquid nitrogen, the differences in coefficients of thermal expansion result in the two flaps 1110a and 1110b bending inwards to clamp the chip section 1120 as illustrated in FIG. 11B. In a particular embodiment, the inside surface of the flaps 1110a and 1110b are coated with a material 1130a and 1130b that is tacky at room temperature (e.g., RTV) to temporarily hold the chip section in place while the flaps reach liquid nitrogen temperatures. Upon thawing to room temperature, the flaps would return to their original state, releasing the grip on the chip section, and allowing the holder to be re-used. FIG. 11C illustrates the embodiment including the tacky material at room temperature. Additional modifications, such as guide lines, are incorporated into the holder to improve the ease with which an end-user would position the chip section in the holder in other embodiments. One of ordinary skill in the art would recognize many variations, modifications, and alternatives.

In a particular embodiment, four metering cells for each reagent were arranged on the carrier such that they could be sliced and removed from the carrier individually. Mounting devices, based upon standard cryo-loop mounting pins as described above, were used to hold the excised chip section. Crystals were cryoprotected in situ by piercing the roof of the protein well or reaction chamber and overlaying the tear with cryoprotectant. Once the cryoprotectant diffused into the well, the sections including the wells or reaction chambers were frozen directly in liquid nitrogen. Subsequent x-ray analysis was performed in situ to identify macromolecular crystals based on diffraction data. Addition analysis may be used to judge the quality of the crystals in situ based on the diffraction data, thereby automating what is generally a labor-intensive manual process.

According to an embodiment of the present invention, a device for supporting a section of an integrated fluidic circuit is provided. The device includes a plurality of flaps extending from a base. Each of the plurality of flaps comprises a first material and a second material, with the first material disposed interior to the second material. The coefficient of thermal expansion of the first material is greater than a coefficient of thermal expansion of the second material. In a particular embodiment, the first material and the second material are generally plate shaped and laminated in a direction normal to the plate surfaces. In a specific embodiment, the device further comprises a third material disposed interior to the second material. The third material is characterized by an adhesion greater than the first material.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An integrated fluidic circuit comprising:
    a substrate including a support surface and a bonding surface opposing the support surface;
    a flow layer coupled to the bonding surface of the substrate and including a flow material characterized by a first thickness, wherein the flow layer defines a plurality of reaction chambers having a height less than the first thickness;
    a control layer coupled to the bonding surface of the substrate and defining a plurality of control structures having a height measured along a normal to the bonding surface, wherein the control layer comprises:
        a first layer of a first material characterized by a first x-ray scattering cross-section and a thickness less than the height; and
        a second layer of a second material characterized by a second x-ray scattering cross-section less than the first x-ray scattering cross-section, the second layer being adjacent the first layer.

2. The integrated fluidic circuit of claim 1 wherein the substrate comprises a cyclic olefin polymer material.

3. The integrated fluidic circuit of claim 1 wherein the plurality of reaction chambers are configured to support macromolecular crystallization processes.

4. The integrated fluidic circuit of claim 1 wherein an aspect ratio of one or more of the plurality of reaction chambers is defined by a height perpendicular to the bonding surface less than a width and length measured in a plane of the bonding surface.

5. The integrated fluidic circuit of claim 1 wherein the flow material and the first material are an elastomeric material including silicon and the second material comprises an elastomeric material substantially free of silicon.

6. The integrated fluidic circuit of claim 5 wherein the elastomeric material including silicon comprises PDMS and the elastomeric material substantially free of silicon comprises polyurethane.

7. The integrated fluidic circuit of claim 5 wherein the flow layer is joined to the bonding surface of the substrate and the control layer is joined to the flow layer.

8. An integrated microfluidic circuit for use in an x-ray diffraction analysis system, the integrated microfluidic circuit comprising:
    a substrate, wherein a normal to the substrate defines an x-ray beam path;
    a flow layer coupled to the substrate and characterized by a first material having a first thickness measured along the x-ray beam path, wherein the flow layer defines a plurality of reaction chambers characterized by a height measured along the x-ray beam path less than the first thickness and a plurality of valves in fluid connection with the plurality of reaction chambers, the plurality of reaction chambers being configured to receive a flow of one or more fluids;
    a control layer coupled to the flow layer and characterized by a second thickness measured along the x-ray beam path, wherein the control layer defines a plurality of control lines characterized by a second height measured along the x-ray beam path less than the second thickness and configured to actuate the plurality of valves, wherein the control layer comprises a second material having a thickness measured along the x-ray beam path less than the second height and a third material having a modulus of elasticity greater than a modulus of elasticity of the first material.

9. The integrated microfluidic circuit of claim 8 wherein the first material comprises an elastomer including silicon and the third material comprises an elastomer substantially free of silicon.

10. The integrated microfluidic circuit of claim 9 wherein the elastomer including silicon comprises PDMS and the elastomer substantially free of silicon comprises a urethane material.

11. The integrated microfluidic circuit of claim 10 wherein the urethane material comprises a urethane blend.

12. The integrated microfluidic circuit of claim 9 wherein the second material comprises PDMS.

13. The integrated microfluidic circuit of claim 8 wherein the height of the plurality of reaction chambers is greater than or equal to about 20 μm and the plurality of reaction chambers are characterized by an aspect ratio of height:width:length of 1:x:y, where at least one of x or y are greater than six.

14. The integrated microfluidic circuit of claim 13 where at least one of x or y are greater than 25.

15. The integrated microfluidic circuit of claim 8 wherein the x-ray diffraction analysis system comprises:
    an x-ray source configured to provide an x-ray beam along the x-ray beam path;
    a detector configured to receive x-rays scattered from one or more crystals present in one of the plurality of reaction chambers;
    a processor coupled to the detector; and
    a controller coupled to the processor.

16. The integrated microfluidic circuit of claim 15 wherein the crystals comprise macromolecular crystals.

17. An integrated fluidic circuit comprising:
a substrate layer;
a first structure coupled to the substrate layer and including a plurality of channels, wherein the first structure is configured to provide for flow of one or more materials through the plurality of channels; and
a second structure coupled to the substrate layer and including a plurality of control channels having a height and configured to receive an actuation pressure, wherein the second structure comprises a first portion having a first portion thickness less than the height and a second portion overlying the first portion and wherein the integrated fluidic circuit is characterized by a thickness of less than 1.5 mm.

18. The integrated fluidic circuit of claim 17 wherein the integrated fluidic circuit is characterized by a thickness of less than 500 μm.

19. The integrated fluidic circuit of claim 18 wherein the integrated fluidic circuit is characterized by a thickness of less than 350 μm.

20. The integrated fluidic circuit of claim 17 wherein the first structure comprises a first elastomeric layer and the first portion of the second structure comprises a layer of the first elastomeric material and the second portion comprises a layer of a second material.

21. The integrated fluidic circuit of claim 20 wherein the second material comprises a polyurethane material.

22. The integrated fluidic circuit of claim 17 wherein the first structure is joined to the substrate layer and the second structure is joined to the first structure.

23. The integrated fluidic circuit of claim 17 wherein the first structure is characterized by a first thickness and includes one or more molded features characterized by a first mold height, wherein the first thickness is less than ten times the first mold height.

24. The integrated fluidic circuit of claim 17 wherein the second structure is characterized by a second thickness less than ten times the height.

25. The integrated fluidic circuit of claim 17 wherein the first structure includes one or more molded features having a first mold height and the height is less than three times the first mold height.

26. The integrated fluidic circuit of claim 17 wherein the first structure is characterized by a thickness of less than 250 μm and the second structure is characterized by a thickness of less than 500 μm.

* * * * *